(12) United States Patent
Bharate et al.

(10) Patent No.: US 10,696,688 B2
(45) Date of Patent: Jun. 30, 2020

(54) FUSED PYRIMIDINES AS ISOFORM SELECTIVE PHOSPHOINOSITIDE-3-KINASE-ALPHA INHIBITORS AND PROCESS FOR PREPARATION THEREOF

(71) Applicant: Council of Scientific and Industrial Research, New Delhi (IN)

(72) Inventors: Sandip Bibishan Bharate, Jammu (IN); Shashi Bhushan, Jammu (IN); Shabber Mohammed, Jammu (IN); Santosh Kumar Guru, Jammu (IN); Sonali Sandip Bharate, Jammu (IN); Vikas Kumar, Jammu (IN); Girish Mahajan, Jammu (IN); Mubashir Javed Mintoo, Jammu (IN); Dilip Manikrao Mondhe, Jammu (IN); Ram Vishwakarma, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 136 days.

(21) Appl. No.: 15/774,520

(22) PCT Filed: Nov. 21, 2016

(86) PCT No.: PCT/IN2016/050416
§ 371 (c)(1),
(2) Date: May 8, 2018

(87) PCT Pub. No.: WO2017/090058
PCT Pub. Date: Jun. 1, 2017

(65) Prior Publication Data
US 2020/0031845 A1    Jan. 30, 2020

(30) Foreign Application Priority Data
Nov. 23, 2015 (IN) .......................... 3818/DEL/2015

(51) Int. Cl.
C07D 493/04 (2006.01)
C07D 495/04 (2006.01)
C07D 471/14 (2006.01)

(52) U.S. Cl.
CPC ......... C07D 495/04 (2013.01); C07D 471/14 (2013.01); C07D 493/04 (2013.01)

(58) Field of Classification Search
CPC .......................... C07D 495/04; C07D 493/04
See application file for complete search history.

(56) References Cited

U.S. PATENT DOCUMENTS 3,475,429 A   10/1969  Woitun et al.
8,461,157 B2 * 6/2013  Cai ..................... C07D 413/14
                                                514/234.2

FOREIGN PATENT DOCUMENTS

| CN | 105820175 A | 8/2016 |
| EP | 1277738 A1 | 1/2003 |
| GB | 1057612 | 2/1967 |
| WO | WO-2010/120994 A2 | 10/2010 |
| WO | WO-2011/029279 A1 | 3/2011 |
| WO | WO-2012/082997 A1 | 6/2012 |

OTHER PUBLICATIONS

S. Brachmann et al., 21 Current Opinion in Cell Biology, 194-198 (2009) (Year: 2009).*
J. Engelman et al., 9 Nature Reviews | Cancer, 550-562 (2009) (Year: 2009).*
International Search Report and Written Opinion for PCT/IN2016/050416, dated Apr. 5, 2017, 12 pages.
P. Mordant, et al., "Dependance on Phosphoinositide 3-Kinase and RAS-RAF Pathways Drive the Activity on RAF265, a Novel RAF/VEGFR2 Inhibitor, and RAD001 (Everolimus) in Combination", American Association for Cancer Research, Molecular Cancer Therapeutics, mct.aacrjournals.org, vol. 9, No. 2, Feb. 2010, pp. 358-368.

(Continued)

*Primary Examiner* — Alexander R Pagano
(74) *Attorney, Agent, or Firm* — Blank Rome LLP

(57) ABSTRACT

The present invention relates to fused pyrimidines of formulae I and II wherein, $R_1$, $R_2$ are as herein described. The present invention particularly relates to isoform selective PI3Kα inhibition and their medicinal use as anticancer agents.

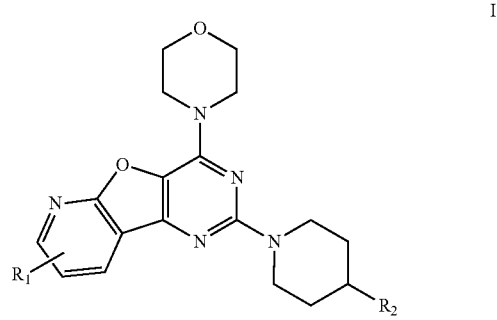

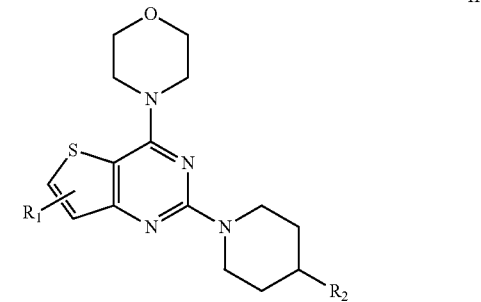

9 Claims, 2 Drawing Sheets

(56) References Cited

OTHER PUBLICATIONS

K. Garber, "Kinase Inhibitors Overachieve in CLL", News & Analysis, Nature Reviews Drug Discovery, www.nature.com/reviews/drugdisc; Feb. 19, 2014, pp. 162-164.

S. B. Bharate, et al., "Kinase Inhibitors of Marine Origin", Chemical Reviews, ACS Publications, pubs.acs.org/CR; 2013 American Chemical Society; Chem. Rev., vol. 113, pp. 6761-6815.

* cited by examiner

FUSED PYRIMIDINES AS ISOFORM SELECTIVE PHOSPHOINOSITIDE-3-KINASE-ALPHA INHIBITORS AND PROCESS FOR PREPARATION THEREOF

RELATED APPLICATIONS

This application is a national phase of PCT/IN2016/050416, filed on Nov. 21, 2016, which claims the benefit of Indian Application No. 3818/DEL/2015, filed on Nov. 23, 2015. The entire contents of those applications are hereby incorporated by reference.

FIELD OF THE INVENTION

The present invention relates to the new series of fused pyrimidines connected with saturated heterocycles. The present invention particularly relates to synthesis, anticancer and phosphoinositide-3-kinase inhibitory activity of fused pyrimidine compounds. More particularly the present invention relates to methods for the treatment of cancer diseases, including those caused by kinase-mediated proliferation of tumor cells. Compounds of the invention can be used for prevention or in the treatment of cancer diseases, such as pancreatic, breast, prostate and melanoma cancers.

BACKGROUND OF THE INVENTION

The search for kinase inhibitors has proven to be a fruitful area for the development of pharmaceutically active substances. As an outcome of extensive drug discovery and development efforts in this area, the first PI3K inhibitor idelalisib (quinazolinone class of compound) has been recently approved by FDA in 2014, as a combination with rituximab for chronic lymphocytic leukaemia (*Nature Rev. Drug Discov.* 2014, 13, 162-164). Another PI3K inhibitor (pan-PI3K inhibitor) buparlisib is in phase III clinical trial for treatment of breast cancer. Other PI3K inhibitors in clinical studies include BEZ-235 and BKM-120 (Phase II, Novartis). AstraZeneca's AZD-6482, which is a PI3K-β inhibitor, has completed Phase I trials for the treatment of thrombosis. Another quinazolinone-based isoform-specific PI3K-δ inhibitor IC-87114 (Calistoga) has entered Phase I clinical trial. Other PI3K inhibitors in clinical trials include D106669 and D87503 (Phase I, Aeterna Zentaris), GDC-0941 (Phase I, Genentech) and PKI-587 (Phase I, Pfizer). In addition, several other PI3K inhibitors are in early stages of clinical trials.

Although large numbers of kinase inhibitors have received FDA-approval, the target selectivity remains a formidable challenge in drug development because almost all approved kinase inhibitor drugs works by competing with ATP for the ATP binding site of the enzyme. Hence, there is a great need for next-generation kinase inhibitors that work through alternative mechanisms such as allosteric inhibition. While recently approved kinase inhibitor drugs offer benefits for cancer treatment, further advances are required to effect tumor selective cell killing, avoid off-target related toxicities and improve survival rates (Bharate, S. B. et al., *Chem. Rev.* 2013, 113, 6761). Amongst the four isoforms of phosphoinositide 3-kinases, particularly the α-isoform has been found to be activated by mutation in several cancers; and therefore discovery of α-isoform selective inhibitor is highly important. PI-103 is a multi-targeted PI3K inhibitor for p110α/β/δ/γ with $IC_{50}$ of 2 nM/3 nM/3 nM/15 nM in cell-free assays, and also inhibits mTOR/DNA-PK with $IC_{50}$ of 30 nM/23 nM. Thus, it does not show any selectivity towards α-isoform compared with β, γ and δ isoforms. Furthermore, PI-103 has very poor aqueous solubility (5 µg/ml) and it undergoes rapid metabolism (via glucuronidation of phenolic hydroxyl group).

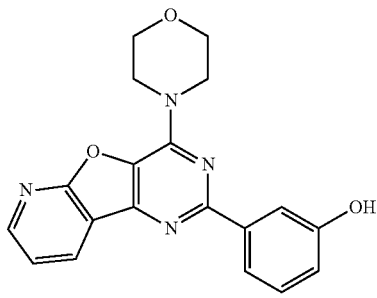

PI-103

OBJECTIVE OF THE INVENTION

An object of the present invention is to provide a new class of compounds as kinase inhibitors, especially as isoform selective PI3K inhibitors, which may be effective in the treatment of cancer associated with PI3K.

Furthermore, another object of the present invention is to provide said compounds, which may be effective in the treatment of immunological, inflammatory, autoimmune, allergic disorders or other diseases or disorders associated with PI3K.

The main object of the present invention is to provide new series of fused pyrimidines connected with saturated heterocycles.

Another object of the present invention is to provide novel isoform selective PI3Kα inhibitors.

One more objective of the invention is to provide a process for preparation of fused pyrimidine class of compounds.

SUMMARY OF THE INVENTION

The present invention provides a pyridofuropyrimidine class of compounds of formula I and thienopyrimidine class of compounds of formula II, or a pharmaceutically accepted salts, solvates, or stereoisomers, or deuterated derivatives, thereof:

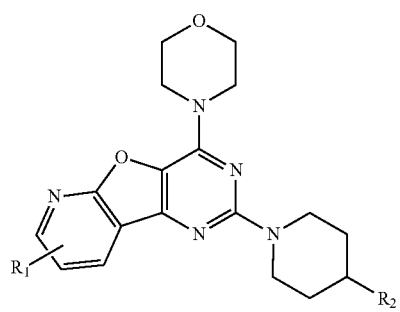

I

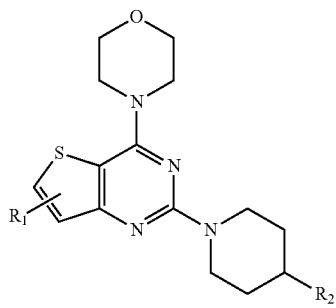

II

Wherein, R₁ may be selected from the groups consisting of hydrogen, halogen, acetyl, alkyl, alkylamino, nitro, sulfonyl, amino, aryl, heteroaryl or fused aryls;
R₂ may be selected from the

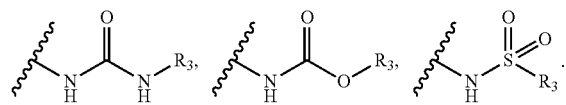

wherein, R₃ may be selected from H, alkyl, aryl, substituted aryl, heteroaryl, substituted heteroaryl, fused aryl or fused heteroaryl.

In yet another embodiment of the invention, substituted phenyl is selected from the group consisting of methyl, nitro, halogens, formyl, vinyl, benzyl, acetyl, hydroxy, phenyl, benzamides alkylphenyls, alkoxyphenyls.

In another embodiment of the invention, alkyl group is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy; or is ($C_5$-$C_8$)-cycloalkyl, ($C_5$-$C_8$)-cycloalkenyl, ($C_6$-$C_{10}$)-bicycloalkyl, ($C_6$-$C_{10}$)-bicycloalkenyl.

In a further embodiment of the invention wherein, the structural formulae of the said compounds comprising:

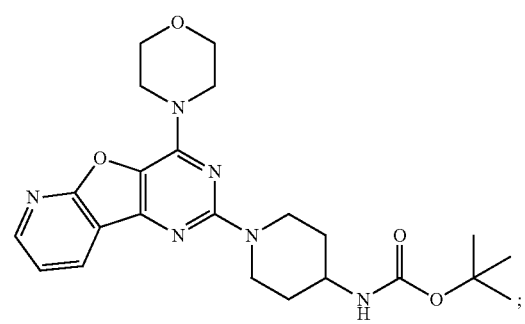

6

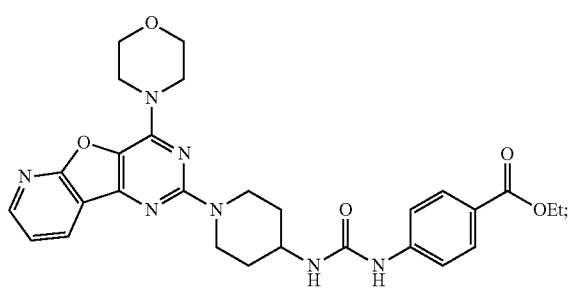

8

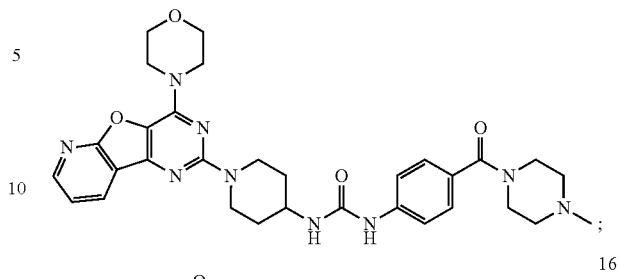

10

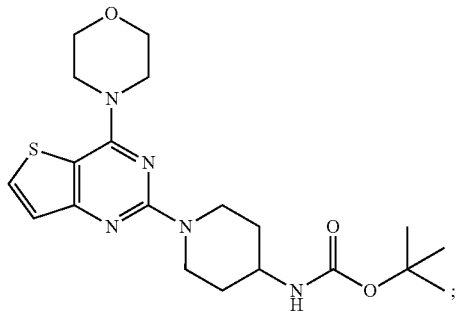

16

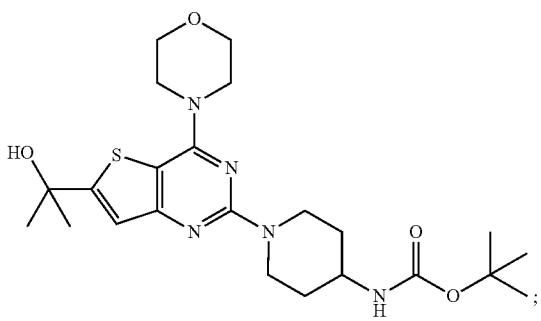

17

21

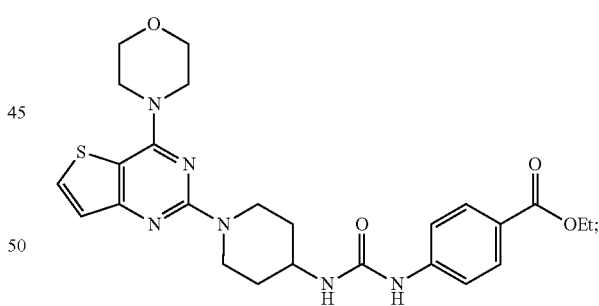

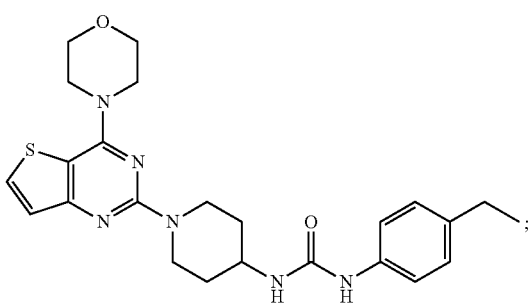

22

-continued

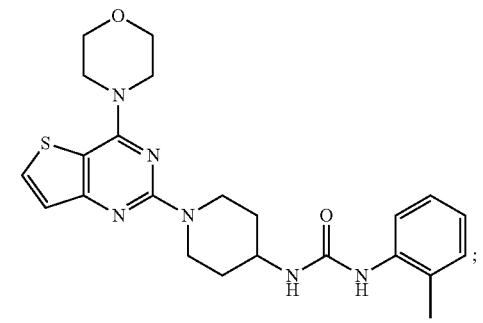
23

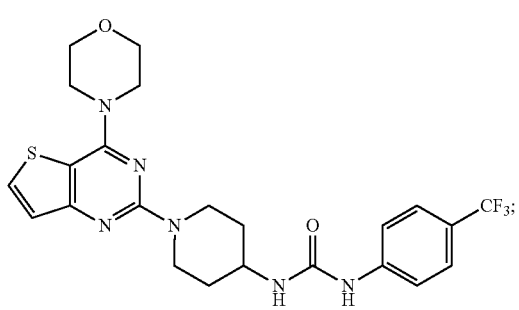
24

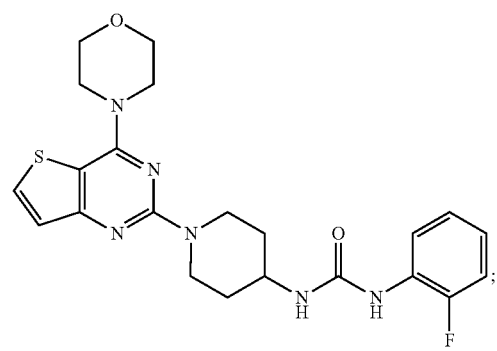
25

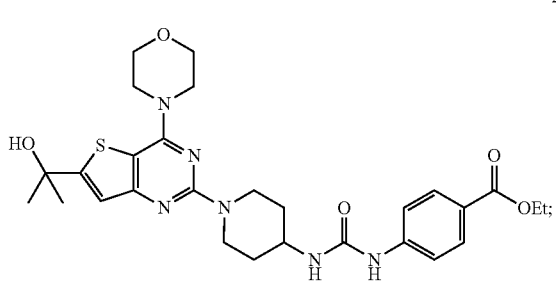
26

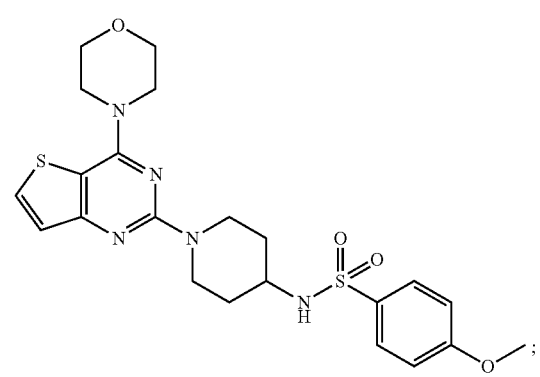
27

-continued

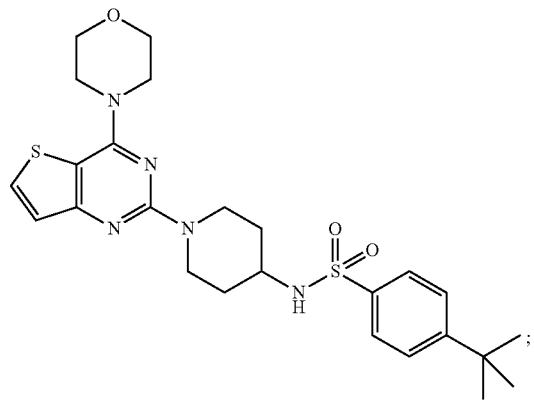
28

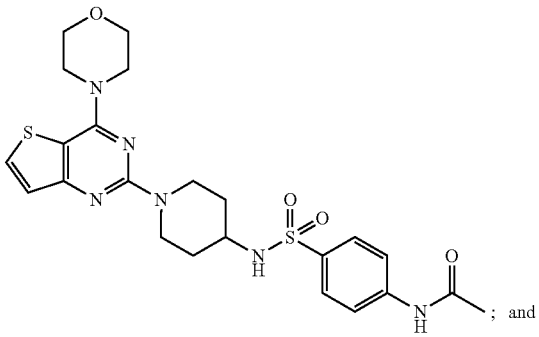
29

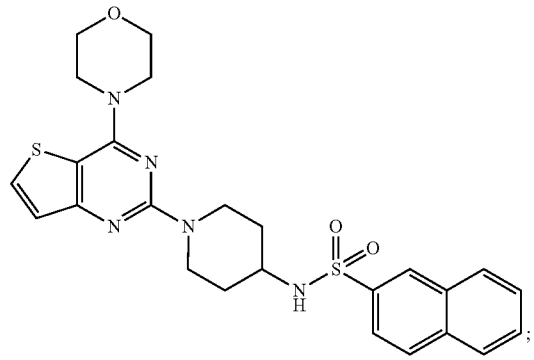
; and

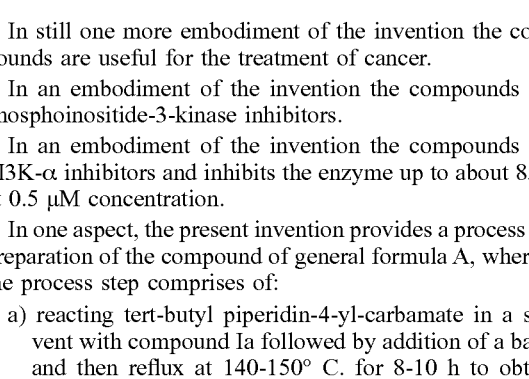
30

In still one more embodiment of the invention the compounds are useful for the treatment of cancer.

In an embodiment of the invention the compounds are phosphoinositide-3-kinase inhibitors.

In an embodiment of the invention the compounds are PI3K-α inhibitors and inhibits the enzyme up to about 85% at 0.5 μM concentration.

In one aspect, the present invention provides a process for preparation of the compound of general formula A, wherein the process step comprises of:

a) reacting tert-butyl piperidin-4-yl-carbamate in a solvent with compound Ia followed by addition of a base, and then reflux at 140-150° C. for 8-10 h to obtain compound IIa;

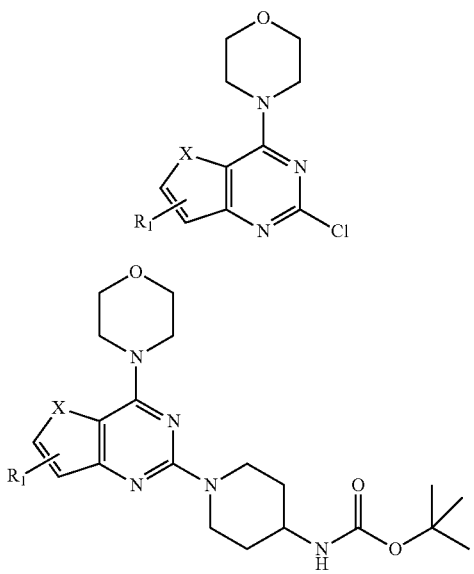

(Ia)

(IIa)

wherein, X=O or S;

R₁ is selected from the group consisting of hydrogen, halogen, acetyl, alkyl, alkylamino, nitro, sulfonyl, amino, aryl, heteroaryl or fused aryls;

b) wherein Alkyl group is selected from the group consisting of $(C_1-C_6)$-alkyl, $(C_1-C_4)$-haloalkyl, $(C_1-C_4)$-alkoxy, $(C_1-C_4)$-haloalkoxy; or is $(C_5-C_8)$-cycloalkyl, $(C_5-C_8)$-cycloalkenyl, $(C_6-C_{10})$-bicycloalkyl, $(C_6-C_{10})$-bicycloalkenyl, treating compound IIa obtained from step (a) with 30% TFA in DCM or chloroform for a period in the range of 1 to 5 h to obtain compound IIIa;

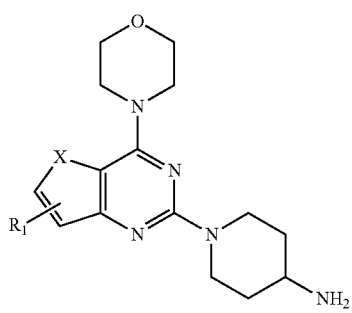

(IIIa)

wherein,
X=O or S;

R₁ is selected from the group consisting of hydrogen, halogen, acetyl, alkyl, alkylamino, nitro, sulfonyl, amino, aryl, heteroaryl or fused aryls;

wherein Alkyl group is selected from the group consisting of $(C_1-C_6)$-alkyl, $(C_1-C_4)$-haloalkyl, $(C_1-C_4)$-alkoxy, $(C_1-C_4)$-haloalkoxy; or is $(C_5-C_8)$-cycloalkyl, $(C_5-C_8)$-cycloalkenyl, $(C_6-C_{10})$-bicycloalkyl, $(C_6-C_{10})$-bicycloalkenyl;

c) reacting ethyl 4-isocyanatobenzoate with compound IIIa obtained from step (b) in a solvent in presence of a base for a period in the range of 1 to 5 h at a temperature ranging between 25 to 40° C. to obtain compound IVa;

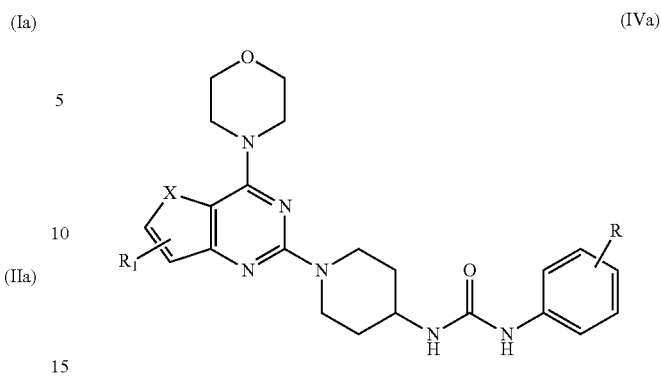

(IVa)

wherein,
X=O or S;

R₁ is selected from the group consisting of hydrogen, halogen, acetyl, alkyl, alkylamino, nitro, sulfonyl, amino, aryl, heteroaryl or fused aryls;

wherein, Alkyl group is selected from the group consisting of $(C_1-C_6)$-alkyl, $(C_1-C_4)$-haloalkyl, $(C_1-C_4)$-alkoxy, $(C_1-C_4)$-haloalkoxy; or is $(C_5-C_8)$-cycloalkyl, $(C_5-C_8)$-cycloalkenyl, $(C_6-C_{10})$-bicycloalkyl, $(C_6-C_{10})$-bicycloalkenyl, wherein, R=4-COOEt, 4-Et, 2-Me, 4-CF₃, 2-F COOH;

d) reacting compounds Ma obtained from step (b) with sulfonyl chlorides in a solvent in presence of a base for a period in the range of 6 to 10 h at a temperature ranging between 25 to 40° C. to obtain compound Va;

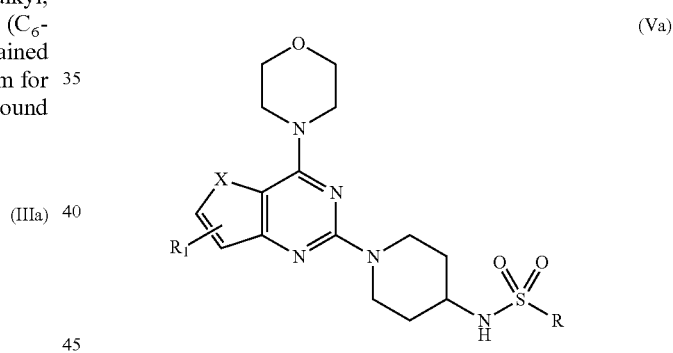

(Va)

wherein,
X=O or S;

R₁ is selected from the group consisting of hydrogen, halogen, acetyl, alkyl, alkylamino, nitro, sulfonyl, amino, aryl, heteroaryl or fused aryls;

wherein Alkyl group is selected from the group consisting of $(C_1-C_6)$-alkyl, $(C_1-C_4)$-haloalkyl, $(C_1-C_4)$-alkoxy, $(C_1-C_4)$-haloalkoxy; or is $(C_5-C_8)$-cycloalkyl, $(C_5-C_8)$-cycloalkenyl, $(C_6-C_{10})$-bicycloalkyl, $(C_6-C_{10})$-bicycloalkenyl, wherein, R=Ph(4-OMe), Ph(4-t-Bu), Ph(4-acetamido) or napthalen-2-yl.

Further, the present invention also provides a process for preparation of the pyrido-fluropyrimidines of general formula I, comprising:

a) condensation of 2-chloro-3-pyridine carbonitrile (1) with ethyl glycolate in presence of Cs₂CO₃, or DBU as a base in an inert atmosphere at 110° C. for time period ranging between 22-24 h, to obtain 3-amino-furo [2,3-b]pyridine-2-carboxylic acid ethyl ester (2).

b) condensation of 3-amino-furo[2,3-b]pyridine-2-carboxylic acid ethyl ester (2) obtained in step (a) with urea at 200-220° C., followed by base treatment, and neutralization with HCl to obtain pyrido[3',2':4,5]furo[3,2-d]pyrimidine-2,4(1H,3H)-dione (3).

c) adding POCl$_3$ or PCl$_5$ to the solution of compound 3 (obtained in step b) followed by reflux at 110° C. for 20-24 h to obtain 2,4-dichloropyrido[3',2':4,5]furo[3,2-d]pyrimidine (4).

d) adding morpholine to the solution of compound 4 (obtained in step c) in dry MeOH and stirring for 2 h at room temperature to obtain compound 5.

e) reacting tert-butyl piperidin-4-yl-carbamate in suitable solvent with compound 5 (obtained in step d) followed by addition of K$_2$CO$_3$ as a base, and then reflux at 140-150° C. for 8-10 h to obtain compound 6.

f) treating compound 6 with 30% TFA in DCM for 2 h to obtain compound 7.

g) reacting ethyl 4-isocyanatobenzoate with compound 7 in DCM and in presence of Et$_3$N as a base for 2 h at room temperature to obtain compound 8.

h) reacting compound 8 with LiOH by refluxing for 8 h and then neutralization with 2N HCl to obtain compound 9.

i) reacting 1-methyl piperazine with compound 9 (as obtained in step h) in NMP followed by addition Hunig's base and HBTU and then stirring for overnight at room temperature to obtain compound 10.

For thienopyrimidine analogs of formulae II, the process of preparation involves:

a) condensation of methyl 3-aminothiophene-2-carboxylate (11) with urea at 200-220° C., followed by base treatment, and then neutralization with HCl to obtain thieno[3,2-d]pyrimidine-2,4(1H,3H)-dione (12);

b) adding POCl$_3$ and PCl$_5$ to the solution of compound 12 (as obtained in step a) followed by reflux at 100-150° C. for 10 h to obtain 2,4-dichloro thieno[3,2-d]pyrimidine (13).

c) adding morpholine to the solution of compound 13 (as obtained in step b) in dry MeOH followed by stirring for 1 h at room temperature to obtain compound 14.

d) treating compound 14 (as obtained in step c) with n-BuLi in dry THF followed by addition of acetone and stirring the mixture for 2 h at −78° C. to obtain compound 15.

e) reacting tert-butyl piperidin-4-yl-carbamate in suitable solvent with compound 14 or 15 (as obtained in step c and d, respectively) followed by addition of K$_2$CO$_3$ as a base followed by reflux at 140-150° C. for 8-10 h to obtain compound 16 and 17.

f) treating compound 16 or 17 with 30% TFA in DCM for 2 h to obtain compounds 18 and 19, respectively.

g) reacting compounds 18 and 19 (as obtained in step f) with isocyanates in DCM and Et$_3$N as a base for 2 h at room temperature to obtain compounds 21-26.

h) reacting compound 18 with sulfonyl chlorides in DCM and Et$_3$N as a base for 2 h at room temperature to obtain compounds 27-30.

In an embodiment of the invention, wherein the isocyanates and sulfonyl chlorides in steps (g and h) is selected form the group consisting of substituted phenyls, substituted biphenyls, substituted naphthyls, substituted heteroaryls, substituted alkyls.

In a further embodiment of the invention the process step (d) is selected.

In the present invention, the inventors have identified new fused pyrimidine analogs as PI3K-α isoform selective inhibitors showing selectivity fold up to >500 versus β, γ and δ isoforms, respectively with excellent aqueous solubility.

Furthermore, the fused pyrimidines with saturated heterocyclic scaffold has never been reported in literature as PI3K-alpha inhibitor.

DETAILED DESCRIPTION OF THE INVENTION

Figure 1:
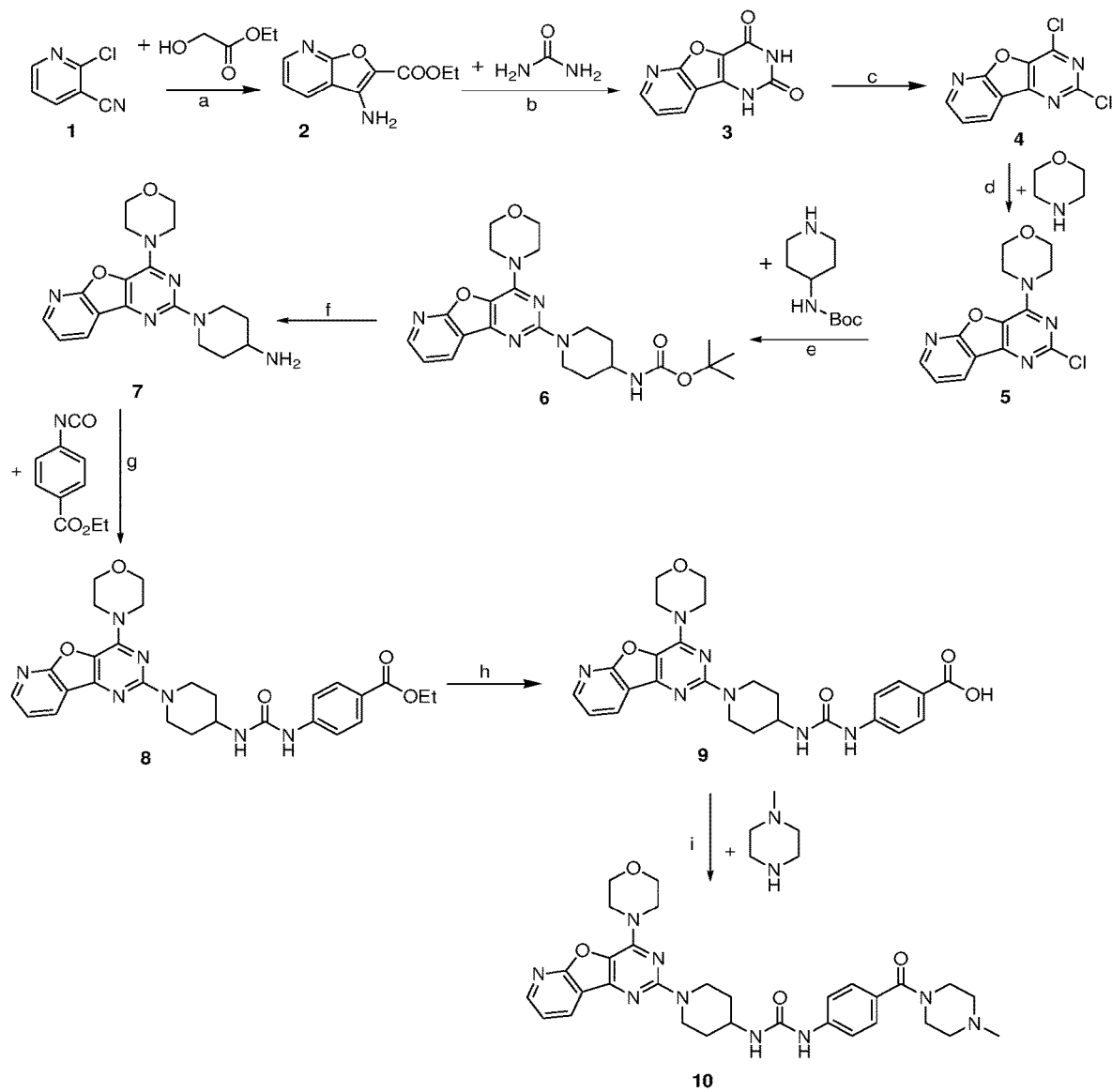
FIG. 1 is a diagram illustrating the chemical synthesis of the pyridopyrimidine analogs of the invention. Reagents and conditions: (a) DBU (2 equiv.), Cs$_2$CO$_3$ (3 equiv.), toluene, reflux, 24 h, 50%; (b) 220° C., urea (5.2 equiv.), 2 h, 60% (c) POCl$_3$ (10 equiv.), PCl$_5$ (4.2 equiv.), reflux at 110° C., 20 h, 71%; (d) morpholine (2.1 equiv.), dry MeOH, rt, 2 h, 99%; (e) K$_2$CO$_3$ (3 equiv.), DMF, 150° C. reflux, 8-10 h, 70%; (f) 30% TFA, DCM, 2 h, rt, 82%; (g) Et$_3$N (1 equiv.), isocyanates (1.2 equiv.), rt, 2 h, 60%; (h) LiOH.3H$_2$O (121 mg, 3 equiv) THF/MeOH/H$_2$O (4:2:1), 8 h, reflux, 63%; (i) Hunig's base (6 equiv), HBTU (5 equiv.), NMP, 1-methyl piperazine (4 equiv.), overnight, rt.
Figure 2:
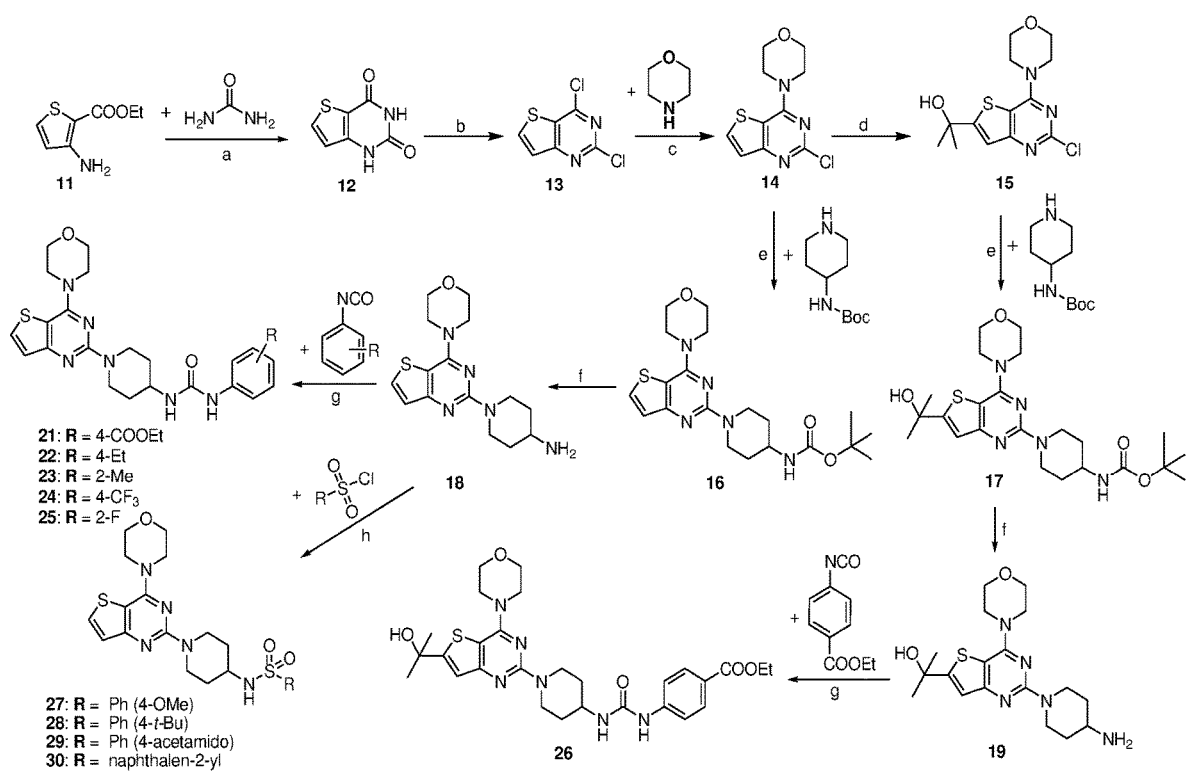
FIG. 2 is a diagram illustrating the chemical synthesis of the thienopyrimidine analogs of the invention. Reagents and conditions: (a) urea (5.2 equiv), 220° C., 150° C., 2 h, 67% (b) POCl$_3$ (10 equiv), reflux at 110° C., 20 h, 70%; (c) morpholine (2.1 equiv), dry MeOH, rt, 1 h, 99%; (d) 2.5 M n-BuLi in hexane (2.2 equiv.), acetone (1.5 equiv), THF, −78° C. to rt, 2 h, 83%; (e) K$_2$CO$_3$ (3 equiv.), DMF, 140° C. reflux, 8-10 h, 73%; (f) 30% TFA, DCM, 2 h, rt, 85%; (g) Et$_3$N (1 equiv), DCM, isocyanates (1.2 equiv.), rt, 60-75%; (h) RSO$_2$Cl (1.2 equiv.), DCM, Et$_3$N (1 equiv.), rt, 55-80%.

The present invention relates to fused pyrimidine class of compounds of general formulae I and II as promising isoform selective PI3K-α inhibitors.

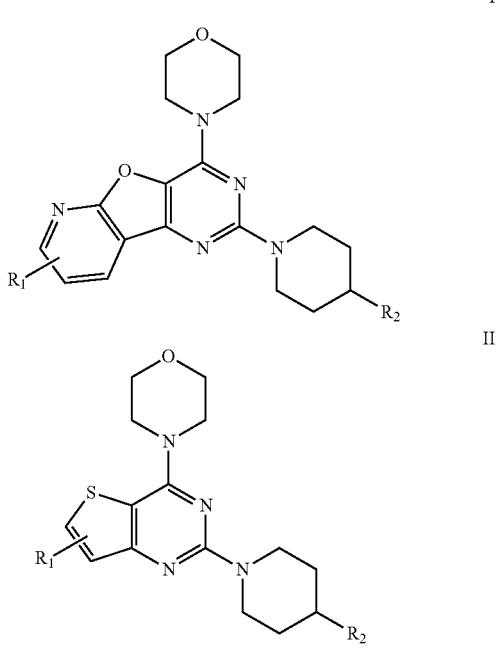

From the series of compounds tested, compounds 8, 10, 17, 22, 24 and 25 showed excellent PI3K-α inhibition. These compounds displayed >70% inhibition of PI3K-α at 500 nM. In addition, compounds 10, 17, 22 and 25 were found to possess excellent aqueous solubility (>200 µg/ml). With these encouraging results, we evaluated IC$_{50}$ values of selected compounds for PI3K-α. Compound 8 and 22 showed PI3K-α inhibition with IC$_{50}$ value of 0.008 and 0.040 µM, respectively. Isoform selectivity was also studied for best 2 compounds. The compound 22 displayed excellent selectivity (>500 fold) towards α-isoform versus other isoforms of PI3K. In particular, the compound 22 did not inhibit (0% inhibition) PI3K-β, -γ, -δ up to 20 µM. Similarly, compound 10 displayed excellent inhibition of PI3K-α and with good aqueous solubility (400 µg/ml). The isoform selectivity of compound 22 towards PI3K-α is provided in the Table 2. The promising PI3K inhibition activity of compound 8 and 22 against PI3K-α clearly indicates their potential to develop as anticancer agents. The inhibitory activity against PI3K-α can therefore be used to treat or prevent diseases, disorders, conditions, or symptoms in a patient (e.g. human) that involve, directly, or indirectly, proliferation of cell growth or over-expression of PI3K-α kinase. A class of fused pyrimidines is presented and defined by structural formulae I and II:

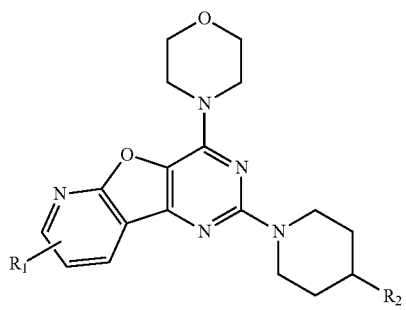

I

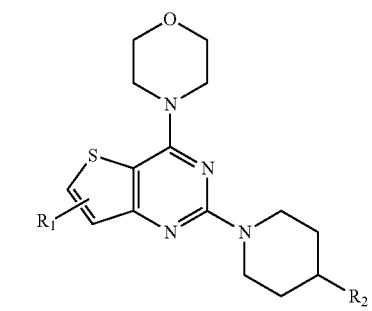

II wherein, R$_1$ may be selected from the groups consisting of hydrogen, halogen, acetyl, alkyl, alkylamino, nitro, sulfonyl, amino, aryl, heteroaryl or fused aryls;
R$_2$ may be selected from the

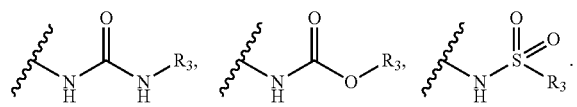

Wherein, R$_3$ may be selected from H, alkyl, alkoxy, substituted aryls, substituted hetero aryls or fused aryls or fused heteroaryls;
Aryl is selected from the group comprising of which are unsubstituted or substituted phenyls, fused aromatics, substituted fused aromatics.

In yet another embodiment of the invention wherein, substituted phenyl may be selected from the group consisting of a methyl, nitro, halogens, formyl, vinyl, benzyl, acetyl, hydroxy, phenyl, benzamides alkylphenyls, alkoxyphenyls.

In another embodiment of the invention wherein Alkyl group is selected from the group consisting of (C$_1$-C$_4$)-haloalkyl, (C$_1$-C$_4$)-alkoxy, (C$_1$-C$_4$)-haloalkoxy; or is (C$_5$-C$_8$)-cycloalkyl, (C$_5$-C$_8$)-cycloalkenyl, (C$_6$-C$_{10}$)-bicycloalkyl, (C$_6$-C$_{10}$)-bicycloalkenyl.

Compounds of the invention derived from formula I and II include, but are not limited to, the following chemical structures:

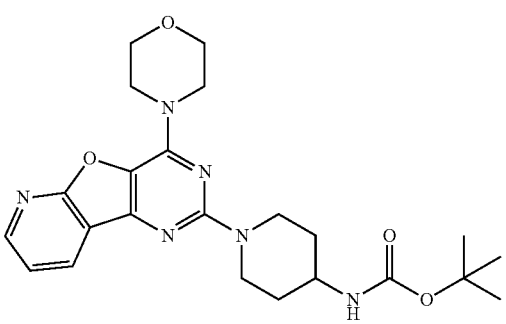 [SMILES: CC(C)(C)OC(=O)NC1CCN(c2nc(N3CCOCC3)c3oc4ncccc4c3n2)CC1]

tert-butyl (1-(4-morpholinopyrido [3',2':4,5]furo[3,2-d]pyrimidin-2-yl)piperidin-4-yl)carbamate (6);

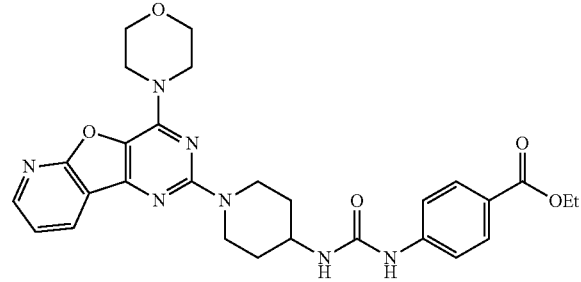 [SMILES: CCOC(=O)c1ccc(NC(=O)NC2CCN(c3nc(N4CCOCC4)c4oc5ncccc5c4n3)CC2)cc1]

ethyl 4-(3-(1-(4-morpholinopyrido[3',2':4,5]furo[3,2-d]pyrimidin-2-yl)piperidin-4-yl)ureido)benzoate, (8);

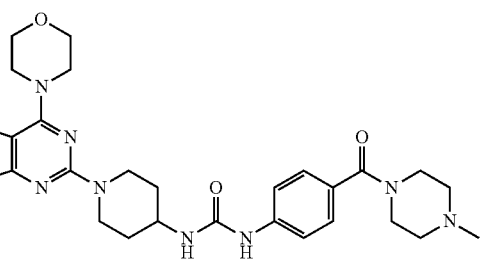

1-(4-(4-methylpiperazine-1-carbonyl)phenyl)-3-(1-(4-morpholinopyrido[3',2':4,5]furo[3,2-d]pyrimidin-2-yl)piperidin-4-yl)urea (10);

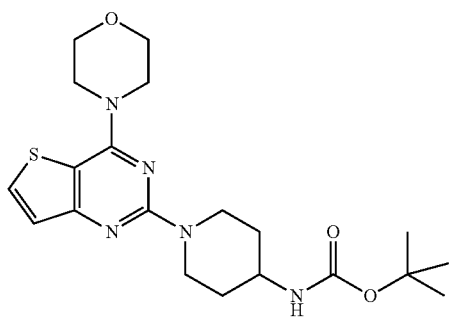 [SMILES: CC(C)(C)OC(=O)NC1CCN(c2nc(N3CCOCC3)c3sccc3n2)CC1]

tert-butyl (1-(4-morpholino thieno[3,2-d]pyrimidin-2-yl)piperidin-4-yl)carbamate (16);

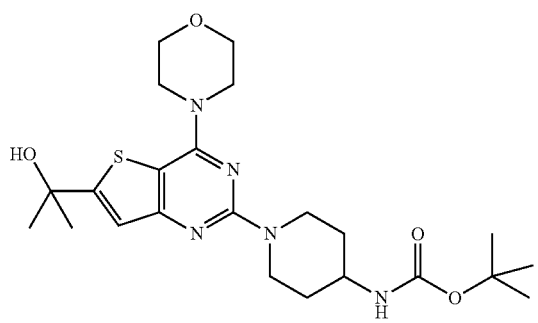 [SMILES: CC(C)(C)OC(=O)NC1CCN(c2nc(N3CCOCC3)c3sc(C(C)(C)O)cc3n2)CC1]

tert-butyl (1-(6-(2-hydroxypropan-2-yl)-4-morpholinothieno[3,2-d]pyrimidin-2-yl)piperidin-4-yl)carbamate (17);

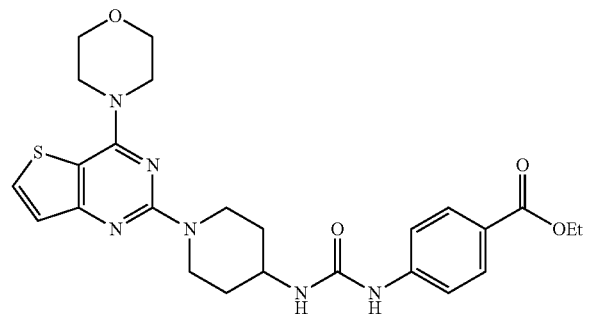 [SMILES: CCOC(=O)c1ccc(NC(=O)NC2CCN(c3nc(N4CCOCC4)c4sccc4n3)CC2)cc1]

ethyl 4-(3-(1-(4-morpholino thieno[3,2-d]pyrimidin-2-yl)piperidin-4-yl)ureido)benzoate (21);

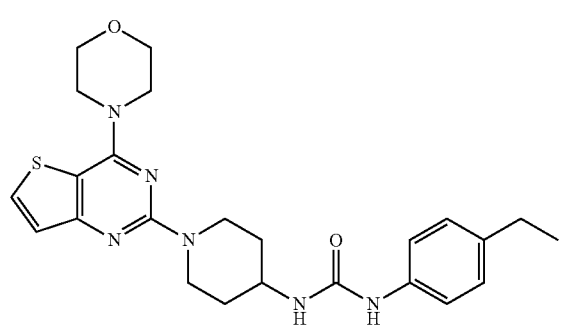 [SMILES: CCc1ccc(NC(=O)NC2CCN(c3nc(N4CCOCC4)c4sccc4n3)CC2)cc1]

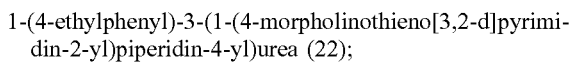

1-(4-ethylphenyl)-3-(1-(4-morpholinothieno[3,2-d]pyrimidin-2-yl)piperidin-4-yl)urea (22);

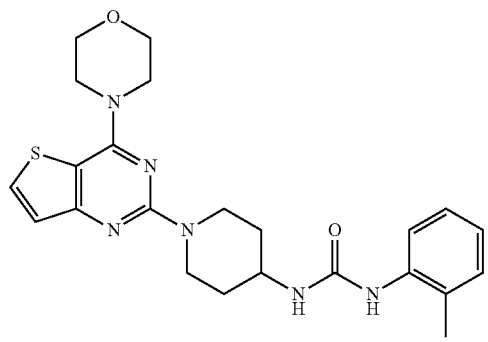 [SMILES: Cc1ccccc1NC(=O)NC1CCN(c2nc(N3CCOCC3)c3sccc3n2)CC1]

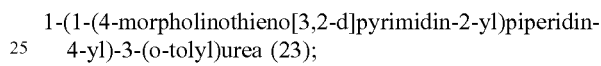

1-(1-(4-morpholinothieno[3,2-d]pyrimidin-2-yl)piperidin-4-yl)-3-(o-tolyl)urea (23);

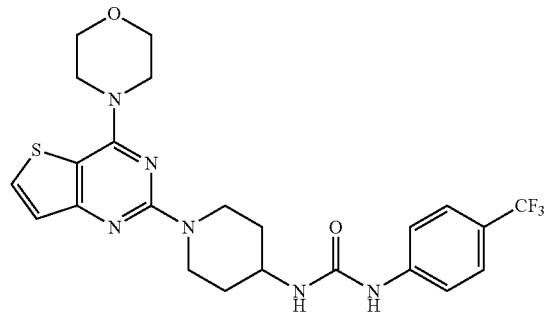 [SMILES: O=C(Nc1ccc(C(F)(F)F)cc1)NC1CCN(c2nc(N3CCOCC3)c3sccc3n2)CC1]

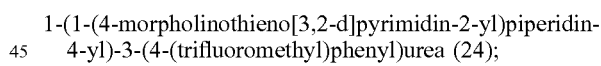

1-(1-(4-morpholinothieno[3,2-d]pyrimidin-2-yl)piperidin-4-yl)-3-(4-(trifluoromethyl)phenyl)urea (24);

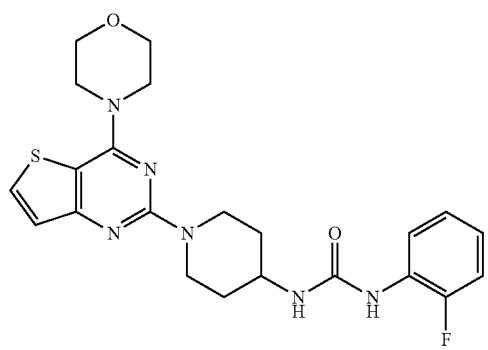 [SMILES: O=C(Nc1ccccc1F)NC1CCN(c2nc(N3CCOCC3)c3sccc3n2)CC1]

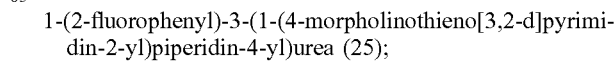

1-(2-fluorophenyl)-3-(1-(4-morpholinothieno[3,2-d]pyrimidin-2-yl)piperidin-4-yl)urea (25);

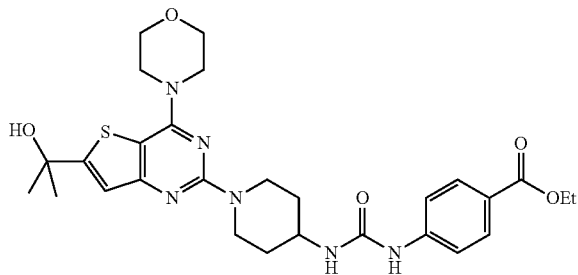 [SMILES: CCOC(=O)c1ccc(NC(=O)NC2CCN(c3nc(N4CCOCC4)c4sc(C(C)(C)O)cc4n3)CC2)cc1]

ethyl 4-(3-(1-(6-(2-hydroxypropan-2-yl)-4-morpholinothieno[3,2-d]pyrimidin-2-yl)piperidin-4-yl)ureido)benzoate (26);

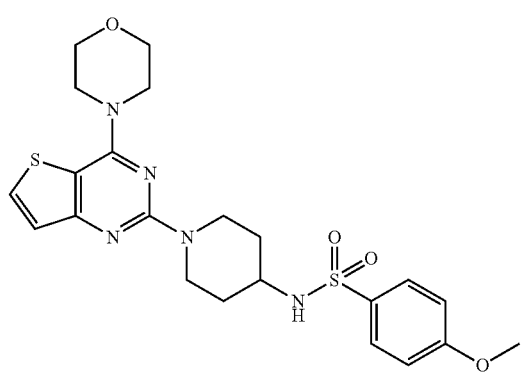 [SMILES: COc1ccc(S(=O)(=O)NC2CCN(c3nc(N4CCOCC4)c4sccc4n3)CC2)cc1]

4-methoxy-N-(1-(4-morpholinothieno[3,2-d]pyrimidin-2-yl)piperidin-4-yl)benzenesulfonamide (27);

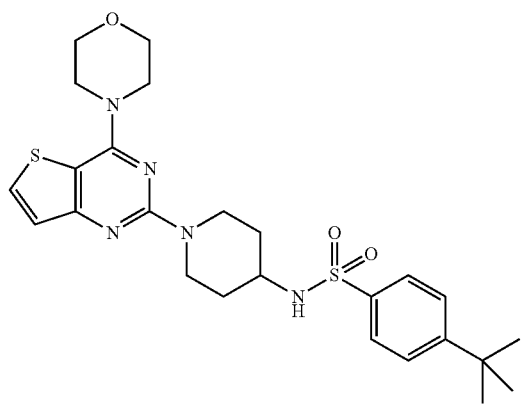 [SMILES: CC(C)(C)c1ccc(S(=O)(=O)NC2CCN(c3nc(N4CCOCC4)c4sccc4n3)CC2)cc1]

4-(tert-butyl)-N-(1-(4-morpholinothieno[3,2-d]pyrimidin-2-yl)piperidin-4-yl)benzenesulfonamide (28);

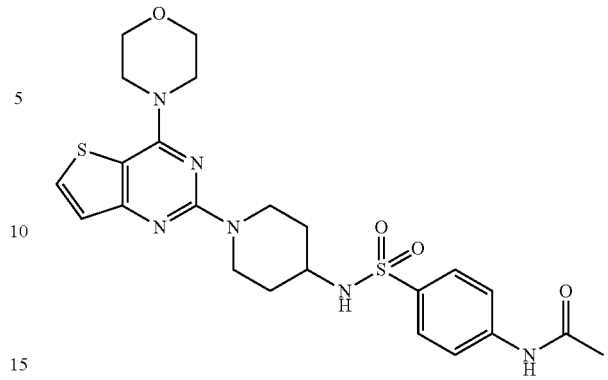

N-(4-(N-(4-(4-morpholino thieno[3,2-d]pyrimidin-2-yl) cyclohexyl) sulfamoyl) phenyl) acetamide (29);

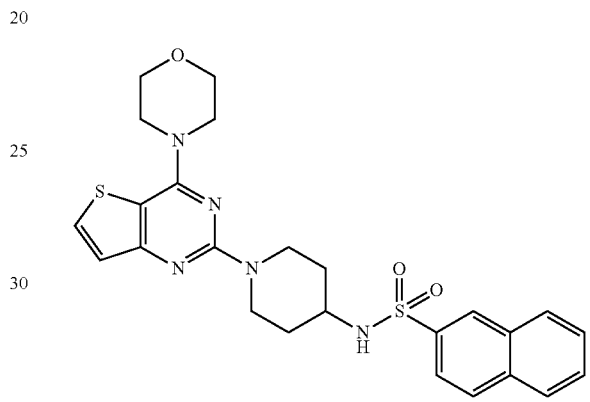

N-(1-(4-morpholino thieno [3,2-d]pyrimidin-2-yl)piperidin-4-yl)naphthalene-2-sulfonamide (30);

As used herein, the terms below have the meanings indicated.

The term "alkoxy," as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term "cancer" as used herein refers to any disease, disorder, condition, or symptom characterized by overexpression of kinases. Cancer diseases include pancreatic, breast, prostate and melanoma cancer.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

Cancer Diseases:

One or more compounds of the invention can be used to treat a patient (e.g. a human) at a risk of developing or already suffering from cancer disease, such as prostate, breast, pancreatic and melanoma cancer.

Methods of Prevention and Treatment:

The compounds of the invention can be used to treat a patient (e.g. a human) that suffers from or is at a risk of suffering from a disease, disorder, condition, or symptom described herein. The compounds of the invention can be used alone or in combination with other agents and compounds in methods of treating or preventing e.g. a cancer disease (e.g. prostate cancer). Each such treatment described above includes the step of administering to a patient in need thereof a therapeutically effective amount of the compound of the invention described herein to delay, reduce or prevent such a disease, disorder, condition, or symptom. The compounds of the invention presented herein may be also useful in reducing growth inhibition of tumors.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Example 1. Synthesis of 3-amino-furo [2,3-b]pyridine-2-carboxylic acid ethyl ester (2)

2-Chloro 3-pyridine carbonitrile (1, 2.0 g, 1 equiv.), $Cs_2CO_3$ (14.2 g, 3 equiv.) and ethyl glycolate (1.5 mL, 1.2 equiv.) were placed in a flask under inert atmosphere. Dry toluene and DBU (4.3 mL, 2 equiv) were added and the suspension was heated at 80° C. for 24 h with vigorous stirring. The reaction mixture was cooled to RT, and then water and EtOAc were added. The organic layer was separated and was washed with water before being dried over anhydrous $Na_2SO_4$ and concentrated in vacuo. Purification was done by column chromatography on silica gel using 10-40% EtOAC: hexane as a mobile phase to get product 2 (1.5 g, 50%) as a white solid. $^1$H NMR ($CDCl_3$, 400 MHz): δ 8.51 (dd, J=5.0, 2.0 Hz, 1H), 7.96 (dd, J=8.0, 2.0 Hz, 1H), 7.23-7.28 (m, 1H), 4.44 (q, J=7.0 Hz, 2H), 4.01 (br, s, 2H), 1.44 (t, J=7.0 Hz, 3H); ESI-MS: m/z 229.05 [M+Na]$^+$.

Example 2. Synthesis of pyrido[3',2':4,5]furo[3,2-d] pyrimidine-2,4(1H,3H)-dione (3)

A mixture of 2 (1.5 g, 1 equiv.) and urea (2.27 g, 5.2 equiv.) was heated at 220° C. for 2 h. The hot reaction mixture was poured onto sodium hydroxide solution and insoluble material was removed by filtration. The mixture was neutralized with 2N HCl and resulting solid was dried to get compound 3 as a gray solid (1.2 g, 77%) by filtration and dried. $^1$H NMR (DMSO-$d_6$, 400 MHz): δ 12.06 (br, 1H), 11.49 (br, 1H), 8.60 (dd, J=5.0, 1.5 Hz, 1H), 8.43 (dd, J=8.0, 2.0 Hz, 1H), 7.56 (dd, J=8.0, 5.0 Hz, 1H); ESI-MS: m/z 202 [M−H]$^-$.

Example 3. Synthesis of 2,4-dichloropyrido[3',2':4, 5]furo[3,2-d]pyrimidine (4)

To the mixture of compound 3 (1.2 g, 1 equiv.) and $PCl_5$ (5.11 g, 4.2 equiv.) under inert gas, was added $POCl_3$ (8.9 mL, 10 equiv.) and the resulting mixture solution was heated to reflux for 20 h. Mixture was then cooled to room temperature, and was concentrated under reduced pressure. Residue was diluted with $CH_2Cl_2$ and 50 ml chilled water. The aqueous phase was then extracted with $CH_2Cl_2$ (3×20 ml). The combined organic layer was then subsequently dried over anhydrous $Na_2SO_4$ and was concentrated in vacuo rotavapor to get 4 (1 g, 71%) as an off-white solid. $^1$H NMR ($CDCl_3$, 400 MHz): δ 8.80 (dd, J=5.0, 1.5 Hz, 1H), 8.64 (dd, J=8.0, 2.0 Hz, 1H), 7.61 (dd, J=7.5, 5.0 Hz, 1H); ESI-MS: m/z 239.97 [M+H]$^+$.

Example 4. Synthesis of 2-chloro-4-morpholinopyrido [3',2':4,5]furo[3,2-d]pyrimidine (5)

To the solution of compound 4 (1 g, 1 equiv.) in dry methanol was added morpholine (0.7 mL, 2.1 equiv) dropwise, and the resulting solution was stirred for 2 h at rt. The resulting precipitate was filtered, then washed with water and a mixture of MeOH/water, and remaining solid was dried in vacuo to furnish product 5 (1.21 g, 100%) as a white solid. $^1$H NMR (CDCl$_3$, 400 MHz): δ 8.63 (dd, J=5.0, 1.5 Hz, 1H), 8.52 (dd, J=8.0, 2.0 Hz, 1H), 7.48 (dd, J=7.5, 5.0 Hz, 1H), 4.23-4.10 (m, 4H), 3.91-3.86 (m, 4H); ESI-MS: m/z 291.06 [M+H]$^+$.

Example 5. Synthesis of tert-butyl (1-(4-morpholinopyrido [3',2':4,5]furo[3,2-d]pyrimidin-2-yl)piperidin-4-yl)carbamate (6)

The mixture of compound 5 (1.2 g, 1 equiv) and tert-butyl piperidin-4-ylcarbamate (1.65 g, 2 equiv) in DMF was heated at 140° C. for 8 h. The mixture was cooled at rt and poured in crushed ice and extracted with EtOAc. The combined organic layer was dried over anhydrous Na$_2$SO$_4$ and was concentrated in vacuo. Purification on silica gel using 10-40% EtOAc: Hexane as a mobile phase furnished compound 6 (1.32 g, 70%) as tan solid. $^1$H NMR (400 MHz, CDCl$_3$): δ 8.51 (d, J=4.3 Hz, 1H), 8.39 (d, J=7.5 Hz, 1H), 7.35 (dd, J=6.9, 5.0 Hz, 1H), 4.67 (d, J=13.2 Hz, 2H), 4.48 (s, 1H), 4.08-4.01 (m, 4H), 3.86-3.72 (m, 6H), 3.05 (t, J=11.4 Hz, 2H), 2.04 (d, J=9.9 Hz, 2H), 1.46 (s, 9H); $^{13}$C NMR (CDCl$_3$, 100 MHz): δ 162.7, 158.7, 155.2, 149.2, 148.8, 131.4, 129.1, 119.4, 115.4, 66.8, 45.6, 43.6, 32.4, 28.4; ESI-MS: m/z 455.23 [M+H]$^+$.

Example 6. Synthesis of 1-(4-morpholinopyrido [3',2':4,5]furo[3,2-d]pyrimidin-2-yl)piperidin-4-amine (7)

To the solution of compound 6 (1.2 g, 1 equiv.) in CH$_2$Cl$_2$ was added 30% TFA in CH$_2$Cl$_2$ solution and reaction mixture was stirred at rt for 2 h. The reaction mixture was poured onto crushed ice and basified with NaOH solution. Then aqueous solution was then extracted with CH$_2$Cl$_2$. The combined organic layer was dried over anhydrous Na$_2$SO$_4$ and was concentrated in vacuo. The obtained crude product 7 (0.75 g, 82%) was used directly for next step.

Example 7. Synthesis of ethyl 4-(3-(1-(4-morpholinopyrido[3',2':4,5]furo[3,2-d]pyrimidin-2-yl) piperidin-4-yl)ureido)benzoate (8)

To the solution of compound 7 (400 mg, 1 equiv) in CH$_2$Cl$_2$ was added Et$_3$N (0.1 mL, 1 equiv.) and ethyl 4-isocyanatobenzoate (258 mg, 1.2 equiv.) and resulting mixture was stirred at rt for 2 h. The resulting precipitate was filtered, and then washed with 10% aqueous MeOH, following by solvent evaporation to get compound 8 as a solid (360 mg, 60%). $^1$H NMR (400 MHz, DMSO-d$_6$, ppm): δ 8.83 (s, 1H), 8.57 (d, J=3.1 Hz, 1H), 8.47 (d, J=7.6 Hz, 1H), 8.32 (s, 1H), 7.84 (d, J=8.7 Hz, 2H), 7.53-7.49 (m, 3H), 6.40 (d, J=7.4 Hz, 1H), 4.54 (d, J=12.0 Hz, 2H), 4.27 (d, J=7.1 Hz, 2H), 3.95 (s, 4H), 3.79 (s, 4H), 3.14 (t, J=11.7 Hz, 2H), 1.92 (d, J=10.1 Hz, 2H), 1.40 (d, J=9.6 Hz, 2H), 1.31 (t, J=7.0 Hz, 3H); ESI-MS: m/z 546.24 [M+H]$^+$; HRMS: m/z 546.2460 calcd for C$_{28}$H$_{31}$N$_7$O$_5$+H$^+$ (546.2459).

Example 8. Synthesis of 4-(3-(1-(4-morpholinopyrido[3',2':4,5]furo[3,2-d]pyrimidin-2-yl)piperidin-4-yl)ureido)benzoic Acid (9)

To the stirred solution of compound 8 (300 mg, 1 equiv.) in 2.5 mL THF/MeOH/H$_2$O (4:2:1) was added LiOH.3H$_2$O (121 mg, 3 equiv). The mixture was then heated under reflux for 8 h and was concentrated on vacuo rotavapor. Water (5 mL) was added, and the mixture was then acidified with 2 N HCl. The solid was filtered, washed with water, and dried to get product 9 (200 mg, 63%) as a tan solid, which was taken to next step without further purification.

Example 9. Synthesis of 1-(4-(4-methylpiperazine-1-carbonyl)phenyl)-3-(1-(4-morpholinopyrido[3',2': 4,5]furo[3,2-d]pyrimidin-2-yl)piperidin-4-yl)urea (10)

A solution of compound 9 (100 mg, 0.297 mmol), Hunig's base (200 µL, 6 equiv.), and HBTU (375 mg, 5 equiv.) in 2 mL NMP was stirred at room temperature for 1 h. 1-Methyl piperazine (77 µl, 4 equiv.) was added, and the mixture was stirred overnight. Dichloromethane (40 mL) was added to the reaction mixture and was washed with saturated NaHCO$_3$ and water. The obtained organic layer was concentrated and purified by silica gel column chromatography using CH$_2$Cl$_2$/methanol/7N NH$_3$ (10:1:0.22) as a mobile phase to get product 10 as a gray solid (35 mg, 31% yield). $^1$H NMR (400 MHz, CDCl$_3$, ppm): δ 8.66 (s, 1H), 8.57 (dd, J=4.8, 1.7 Hz, 1H), 8.47 (dd, J=7.7, 1.6 Hz, 1H), 7.51 (dd, J=7.6, 4.9 Hz, 1H), 7.45 (d, J=8.6 Hz, 2H), 7.29 (d, J=8.5 Hz, 2H), 6.35 (d, J=7.7 Hz, 1H), 4.53 (d, J=13.2 Hz, 2H), 3.94 (d, J=4.5 Hz, 5H), 3.79 (d, J=4.6 Hz, 6H), 3.43 (s, 1H), 3.15 (t, J=11.1 Hz, 3H), 2.51 (d, J=1.7 Hz, 4H), 2.39 (s, 4H), 2.25 (s, 3H); $^{13}$C NMR (CDCl$_3$, 100 MHz): δ 169.6, 162.6, 158.6, 154.8, 149.6, 149.2, 147.8, 142.4, 131.8, 128.7, 128.0, 120.5, 117.2, 115.0, 79.6, 66.4, 47.0, 45.6, 43.3, 32.3, 29.4, 22.5; ESI-MS: m/z 600.21 [M+H]$^+$.

Example 10. Synthesis of thieno[3,2-d]pyrimidine-2,4(1H,3H)-dione (12)

A mixture of methyl 3-aminothiophene-2-carboxylate (11, 13.48 g, 1 equiv.) and urea (26.75 g, 5.2 equiv.) was heated at 220° C. for 2 h. The hot reaction mixture was poured into sodium hydroxide solution and insoluble material was removed by filtration. The mixture was then neutralized with 2N HCl to get grey solid of compound 12 (9.62 g, 67%). $^1$H NMR (400 MHz, DMSO-d$_6$, ppm): δ 11.60 (s, 1H), 11.19 (d, J=14.0 Hz, 1H), 8.04 (d, J=4.0 Hz, 1H), 6.92 (d, J=4.0 Hz, 1H); ESI-MS: m/z 169.12 [M+H]$^+$.

Example 11. Synthesis of 2,4-dichloro thieno[3,2-d]pyrimidine (13)

A mixture of compound 12 (8.68 g, 56.49 m mol) and POCl$_3$ (150 mL) was heated at reflux for 10 h. After completion of the reaction, reaction mixture was concentrated to half of the initial volume. Then, it was poured onto child ice with vigorous stirring to get compound 13 (7.42 g, 70%) as white solid. $^1$H NMR (400 MHz, CDCl$_3$, ppm): δ 8.05 (d, J=5.6 Hz, 1H), 7.48 (d, J=5.6 Hz, 1H); ESI-MS: m/z 205.05 [M+H]$^+$.

Example 12. Synthesis of 4-(2-chloro thieno[3,2-d]pyrimidin-4-yl)morpholine

A mixture of compound 13 (7.42, 1 equiv.) and morpholine (7.11 mL, 2.2 equiv) in methanol (150 mL) was stirred at rt for 1 h. The resulting precipitate was filtered, and then washed with water (3×50 ml) and remaining solid was dried in vacuo to furnish compound 14 (9.09 g, 99%) as white solid. 1H NMR (400 MHz, DMSO-$d_6$, ppm): δ 8.31 (d, J=5.6 Hz, 1H), 7.41 (d, J=5.6 Hz, 1H), 3.91 (t, J=4.8 Hz, 4H), 3.76 (t, J=4.8 Hz, 4H); ESI-MS: m/z 256.72 [M+H]$^+$.

Example 13. Synthesis of 2-(2-chloro-4-morpholino thieno[3,2-d]pyrimidin-6-yl)propan-2-ol (15)

A solution of compound 14 (2.0 g, 1 mmol) in THF (30 mL) was cooled to −78° C. prior to slow addition of 2.5 M n-BuLi in hexane (4.6 mL) via an addition funnel to maintain a temperature below −70° C. The reaction was brought to −60° C. and allowed to stir for 1 h. The reaction mixture was re-cooled to −78° C. and acetone was added slowly via an addition funnel to maintain the temperature below −70° C. After stirring for 2 h, the reaction was quenched with 1 N HCl (10 mL), water (60 g), and ice (60 g). The slurry was filtered and washed with water (15 mL) and dried in a vacuum oven overnight at 50° C. to get 2.08 g of compound 15 (83.5% yield). $^1$H NMR (400 MHz, CDCl$_3$) δ 7.13 (s, 1H), 4.02-3.98 (m, 4H), 3.85-3.82 (m, 4H), 1.71 (s, 6H); ESI-MS: m/z 314.80 [M+H]$^+$.

Example 14. Synthesis of tert-butyl (1-(4-morpholino thieno[3,2-d]pyrimidin-2-yl)piperidin-4-yl) carbamate (16)

The mixture of compound 14 (1 equiv.) and tert-butyl piperidin-4-yl-carbamate (2 equiv.) in DMF was heated at 140° C. at 8 h. The mixture was cooled to rt and poured in crushed ice and was extracted with EtOAc. The combined organic layer was dried over anhydrous Na$_2$SO$_4$ and was concentrated in vacuo. Purification on silica gel using 10-40% EtOAc: Hexane as mobile phase furnished titled compound 16 (70% yield). $^1$H NMR (400 MHz, CDCl$_3$): δ 7.58 (d, J=5.5 Hz, 1H), 7.16 (d, J=4.9 Hz, 1H), 4.64 (d, J=13.1 Hz, 2H), 4.46 (s, 1H), 3.89-3.83 (m, 8H), 3.70 (s, 1H), 3.03 (t, J=11.8 Hz, 2H), 2.01 (d, J=10.6 Hz, 2H), 1.46 (s, 9H); $^{13}$C NMR (CDCl$_3$, 100 MHz): δ 163.8, 160.0, 158.6, 155.2, 131.3, 124.1, 106.0, 79.3, 66.7, 48.4, 46.2, 43.3, 32.4, 29.7, 28.4; ESI-MS: m/z 420.2 [M+H]$^+$.

Example 15. Synthesis of tert-butyl (1-(6-(2-hydroxypropan-2-yl)-4-morpholinothieno[3,2-d]pyrimidin-2-yl)piperidin-4-yl)carbamate (17)

The mixture of compound 15 (1 equiv.) and tert-butyl piperidin-4-yl-carbamate (2 equiv.) in DMF was heated at 140° C. for 8 h. The mixture was cooled to rt and poured in crushed ice and extracted with EtOAc. The combined organic layer was dried over anhydrous Na$_2$SO$_4$ and concentrated in vacuo. Purification on silica gel using 10-40% EtOAc: Hexane as mobile phase furnished titled compound 17 (73% yield). $^1$H NMR (400 MHz, CDCl$_3$): δ 6.99 (s, 1H), 4.62 (d, J=13.6 Hz, 2H), 4.45 (s, 1H), 3.85 (dd, J=16.3, 5.0 Hz, 8H), 3.69 (s, 1H), 3.01 (t, J=11.7 Hz, 2H), 2.14-1.97 (m, 3H), 1.68 (s, 6H), 1.45 (s, 9H); $^{13}$C NMR (CDCl$_3$, 100 MHz): δ 163.9, 160.5, 159.9, 158.4, 155.2, 118.9, 104.4, 79.4, 71.8, 66.8, 48.4, 46.2, 43.3, 32.4, 31.8, 28.4; ESI-MS: m/z 478.24 [M+H]$^+$, HRMS: m/z 478.2474 calcd for C$_{23}$H$_{35}$N$_5$O$_4$S+H$^+$ (478.2483).

Example 16. Synthesis of 1-(4-morpholino thieno[3,2-d]pyrimidin-2-yl)piperidin-4-amine (18)

To the solution of compound 16 (1.2 g, 1 equiv.) in CH$_2$Cl$_2$ was added 30% TFA (in CH$_2$Cl$_2$) solution and resulting mixture was stirred at rt for 2 h. The reaction mixture was poured in crushed ice and basified with NaOH solution. Then, aqueous solution was extracted with CH$_2$Cl$_2$ at pH=8. The combined organic layer was dried over anhydrous Na$_2$SO$_4$ and concentrated in vacuo to get product 18 (0.8 g, 85%). Compound 18 was used for next step without further purification.

Example 17. Synthesis of 2-(2-(4-aminopiperidin-1-yl)-4-morpholino thieno[3,2-d]pyrimidin-6-yl)propan-2-ol (19)

To the solution of compound 17 in CH$_2$Cl$_2$ was added 30% TFA solution (in CH$_2$Cl$_2$) and resulting mixture was stirred at rt for 2 h. The reaction mixture was poured in crushed ice and basified with NaOH solution. Then aqueous solution was extracted with CH$_2$Cl$_2$ at pH=8. The combined organic layer was dried over anhydrous Na$_2$SO$_4$ and was concentrated in vacuo to get compound 19 (80% yield). It was used in next step without further purification.

Example 18. Synthesis of ethyl 4-(3-(1-(4-morpholino thieno[3,2-d]pyrimidin-2-yl)piperidin-4-yl) ureido)benzoate (21)

To the solution of compound 18 (1 equiv.) in CH$_2$Cl$_2$ was added Et$_3$N and ethyl 4-isocyanatobenzoate (1 equiv.) and resulting mixture was stirred for at rt for 1 h. The resulting precipitate was filtered, and was washed with 10% aqueous MeOH. Remaining solid was dried in vacuo to get product 21 (74% yield). White tan solid; $^1$H NMR (400 MHz, DMSO-$d_6$): δ 8.80 (s, 1H), 8.02 (d, J=5.5 Hz, 1H), 7.83 (d, J=8.6 Hz, 2H), 7.51 (d, J=8.7 Hz, 2H), 7.15 (d, J=5.5 Hz, 1H), 6.36 (d, J=7.6 Hz, 1H), 4.48 (d, J=13.2 Hz, 3H), 4.26 (q, J=7.1 Hz, 3H), 3.81-3.73 (m, 8H), 3.09 (t, J=11.2 Hz, 2H), 1.88 (d, J=10.1 Hz, 3H), 1.30 (t, J=8.2 Hz, 3H); $^{13}$C NMR (CDCl$_3$, 100 MHz): δ 168.4, 164.7, 161.2, 159.9, 156.6, 145.7, 133.2, 132.0, 124.7, 118.6, 106.6, 68.0, 62.2, 48.5, 47.6, 44.6, 33.6, 15.4; ESI-MS: m/z 511.22 [M+H]$^+$; HRMS: m/z 511.2118 calcd for C$_{25}$H$_{31}$N$_6$O$_4$S+H$^+$ (511.2122).

Example 19. Synthesis of 1-(4-ethylphenyl)-3-(1-(4-morpholinothieno[3,2-d]pyrimidin-2-yl)piperidin-4-yl)urea (22)

This compound was synthesized using the similar procedure as described in example 17. Yield: 72%; White tan solid; $^1$H NMR (400 MHz, DMSO-$d_6$): δ 7.76-7.67 (m, 1H), 7.25 (d, J=8.1 Hz, 2H), 7.18-7.14 (m, 1H), 7.09 (d, J=8.2 Hz, 2H), 4.55 (d, J=13.4 Hz, 1H), 3.93 (d, J=4.2 Hz, 4H), 3.85 (d, J=4.3 Hz, 5H), 3.16 (t, J=11.3 Hz, 3H), 2.58 (q, J=7.4 Hz, 2H), 2.03 (d, J=12.3 Hz, 2H), 1.50-1.42 (m, 2H), 1.20 (dd, J=9.1, 6.1 Hz, 3H); $^{13}$C NMR (CDCl$_3$, 100 MHz): δ 164.8, 161.2, 159.9, 157.6, 139.9, 138.1, 133.1, 129.5, 124.8, 120.9, 106.6, 68.0, 48.5, 47.6, 44.7, 33.7, 29.4, 16.9; ESI-MS: m/z 467.2 [M+H]$^+$.

Example 20. Synthesis of 1-(1-(4-morpholinothieno[3,2-d]pyrimidin-2-yl)piperidin-4-yl)-3-(o-tolyl)urea (23)

This compound was synthesized using the similar procedure as described in example 17. Yield: 75%; white tan solid; $^1$H NMR (400 MHz, DMSO-$d_6$:) δ 7.76-7.71 (m, 1H), 7.61 (d, J=7.7 Hz, 1H), 7.18-7.12 (m, 3H), 6.98 (t, J=7.1 Hz, 1H), 4.60-4.42 (m, 2H), 3.93-3.85 (m, 8H), 3.16 (t, J=12.2

Hz, 3H), 2.25 (s, 3H), 2.03 (d, J=12.4 Hz, 2H), 1.51-1.42 (m, 2H); ESI-MS: m/z 453.20 [M+H]$^+$; HR-ESIMS: m/z 453.2069 calcd for $C_{23}H_{28}N_6O_2S+H^+$ (453.2067).

Example 21. Synthesis of 1-(1-(4-morpholinothieno [3,2-d]pyrimidin-2-yl)piperidin-4-yl)-3-(4-(trifluoromethyl)phenyl)urea (24)

This compound was synthesized using the similar procedure as described in example 17. Yield: 74%; White tan solid; $^1$H NMR (400 MHz, DMSO): δ 8.80 (s, 1H), 8.02 (d, J=5.5 Hz, 1H), 7.83 (d, J=8.6 Hz, 2H), 7.51 (d, J=8.7 Hz, 2H), 7.15 (d, J=5.5 Hz, 1H), 6.36 (d, J=7.6 Hz, 1H), 4.48 (d, J=13.2 Hz, 2H), 4.26 (s, 1H), 3.83-3.74 (m, 8H), 3.09 (t, J=11.2 Hz, 2H), 1.88 (d, J=10.1 Hz, 3H); ESI-MS: m/z 523.17 [M+H]$^+$.

Example 22. Synthesis of 1-(2-fluorophenyl)-3-(1-(4-morpholinothieno[3,2-d]pyrimidin-2-yl)piperidin-4-yl)urea (25)

This compound was synthesized using the similar procedure as described in example 17. Yield: 74%; White tan solid; $^1$H NMR (400 MHz, DMSO-d$_6$): δ 8.05 (t, J=7.0 Hz, 1H), 7.80-7.58 (m, 2H), 7.21-6.92 (m, 4H), 4.53 (d, J=11.8 Hz, 1H), 3.94-3.86 (m, 8H), 3.34-3.17 (m, 5H), 2.04 (d, J=8.8 Hz, 2H), 1.48 (d, J=9.8 Hz, 2H); ESI-MS: m/z 457.17 [M+H]$^+$; HR-ESIMS: m/z 457.1821 calcd for $C_{22}H_{25}FN_6O_2S+H^+$ (457.1816).

Example 23. Synthesis of ethyl 4-(3-(1-(6-(2-hydroxypropan-2-yl)-4-morpholinothieno[3,2-d]pyrimidin-2-yl)piperidin-4-yl)ureido)benzoate (26)

This compound was synthesized using the similar procedure as described in example 17. Yield: 60%; White tan solid; $^1$H NMR (400 MHz, CDCl$_3$): δ 8.02 (d, J=5.5 Hz, 1H), 7.83 (d, J=8.6 Hz, 2H), 6.99 (s, 1H), 4.48 (d, J=13.2 Hz, 3H), 4.26 (q, J=7.1 Hz, 3H), 3.83-3.74 (m, 8H), 3.09 (t, J=11.2 Hz, 2H), 1.88 (d, J=10.1 Hz, 3H), 1.71 (s, 6H), 1.30 (t, J=8.2 Hz, 3H); ESI-MS: m/z 569.25 [M+H]$^+$; HRMS: m/z 569.2548 calcd for $C_{28}H_{36}N_6O_5S+H^+$ (569.2541).

Example 24. Synthesis of 4-methoxy-N-(1-(4-morpholinothieno[3,2-d]pyrimidin-2-yl)piperidin-4-yl) benzenesulfonamide (27)

To the solution of compound 18 (1 equiv.) in CH$_2$Cl$_2$ was added Et$_3$N and corresponding sulphonyl chloride (1.2 equiv.) and resulting reaction mixture was stirred at rt for 1 h. Reaction mixture was washed with brine solution and organic layer was concentrated on vacuo rotavapor. Purification was done by silica gel column chromatography using 1% MeOH: CH$_2$Cl$_2$ as a mobile phase to get compound 27. Yield: 80%; White solid; $^1$H NMR (400 MHz, CDCl$_3$) δ 7.88-7.81 (m, 2H), 7.61-7.55 (m, 1H), 7.13 (d, J=5.5 Hz, 1H), 6.99 (d, J=8.9 Hz, 2H), 4.51 (d, J=13.1 Hz, 3H), 3.85-3.83 (m, 8H), 3.49 (s, 3H), 3.43-3.33 (m, 1H), 2.99 (t, J=8.2 Hz, 2H), 1.82 (d, J=8.2 Hz, 2H), 1.44-1.36 (m, 2H); $^{13}$C NMR (CDCl$_3$, 100 MHz): δ 164.7, 164.1, 161.5, 159.8, 134.4, 133.1, 130.2, 124.8, 115.6, 106.7, 68.0, 56.8, 52.1, 47.6, 44.5, 33.8; ESI-MS: m/z 490.15 [M+H]$^+$; HRMS: m/z 490.1576 calcd for $C_{22}H_{27}N_5O_4S_2+H^+$ (490.1577).

Example 25. Synthesis of 4-(tert-butyl)-N-(1-(4-morpholinothieno[3,2-d]pyrimidin-2-yl)piperidin-4-yl)benzenesulfonamide (28)

This compound was synthesized using the similar procedure as described in example 23. Yield: 78%; White solid; $^1$H NMR (400 MHz, CDCl$_3$, ppm): δ 7.82 (d, J=8.0 Hz, 2H), 7.58 (d, J=8.0 Hz, 2H), 7.52 (d, J=8.0 Hz, 2H), 7.14 (dd, J=4.0, 1H), 4.49-4.63 (m, 3H), 3.86 (t, J=4.0 Hz, 4H), 3.82 (t, J=4.0 Hz, 4H), 3.42 (m, 1H), 3.01 (t, J=12.2 Hz, 2H), 1.85 (d, J=8 Hz, 2H), 1.41 (d, J=8.0 Hz, 2H), 1.35 (s, 9H); ESI-MS: m/z 516.20 [M+H]$^+$; HR-ESIMS: m/z 516.2097 calcd for $C_{25}H_{34}N_5O_3S_2+H^+$ (516.2098).

Example 26. Synthesis of N-(4-(N-(4-(4-morpholino thieno[3,2-d]pyrimidin-2-yl) cyclohexyl) sulfamoyl) phenyl) acetamide (29)

This compound was synthesized using the similar procedure as described in example 23. Yield: 55%; White solid; $^1$H NMR (400 MHz, CDCl$_3$, ppm): δ 10.33 (s, NH), 8.32 (s, NH), 7.99 (d, J=4 Hz, 2H), 7.76 (s, 3H), 7.62 (d, J=8.0, Hz, 1H), 7.11 (d, J=8.0 Hz 1H), 4.38 (d, J=12.0 Hz, 3H), 3.78-3.71 (m, 9H), 2.91 (t, J=8.2 Hz, 3H), 2.10 (s, 3H), 1.59-1.56 (m, 2H); $^{13}$C NMR (CDCl$_3$, 100 MHz): δ 152.4, 141.3, 136.5, 128.7, 128.0, 125.9, 125.8, 124.6, 123.6, 122.6, 121.5, 111.2, 107.7, 80.8, 44.6; ESI-MS: m/z 516.17 [M+H]$^+$; HR-ESIMS: m/z 517.1687 calcd for $C_{24}H_{29}N_5O_4S_2+H^+$ (517.1686).

Example 27. Synthesis of N-(1-(4-morpholino thieno[3,2-d]pyrimidin-2-yl)piperidin-4-yl)naphthalene-2-sulfonamide (30)

This compound was synthesized using the similar procedure as described in example 23. Yield: 72%; White solid; $^1$H NMR (400 MHz, CDCl$_3$, ppm): δ 10.33 (s, NH), 8.32 (s, NH), 7.99 (d, J=4 Hz, 2H), 7.76 (s, 3H), 7.62 (d, J=8.0, Hz, 1H), 7.11 (d, J=8.0 Hz 1H), 4.38 (d, J=12.0 Hz, 1H), 3.71-3.78 (m, 8H), 2.88-2.94 (m, 2H), 2.10 (s, 3H), 1.56-1.59 (m, 2H), 1.24 (m, 2H); $^{13}$C NMR (CDCl$_3$, 100 MHz): δ 152.4, 141.3, 136.5, 128.7, 128.0, 125.9, 125.8, 124.6, 123.6, 122.6, 121.5, 111.2, 107.7, 80.8, 44.6; ESI-MS: m/z 510.16 [M+H]$^+$.

Example 28. Phosphoinositide-3-Kinase Assay

Compounds proposed in present invention were evaluated for their inhibitory activity on phosphoinositide-3-kinase-α and other isoforms (β, γ and δ). The preliminary screening was performed at 0.5 μM. The protocols used for these bioassays are as follows:

PI3K-α Assay:

PI3K-alpha (diluted in 12.5 mM Glycine-NaOH (pH 8.5), 50 mM KCl, 2.5 mM MgCl$_2$, 1 mM DTT, 0.05% CHAPS) is assayed in total volume of 20 μl containing 12.5 mM glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 80 min after which 20 μl of ADP-Glo reagent is added. After a further incubation of 40 min, 40 μl of Kinase Detection Buffer is added. The assays are incubated for 40 min and then read on PerkinElmer Envision for 1 sec/well.

PI3K-β Assay:

PI3K-beta (diluted in 12.5 mM glycine-NaOH (pH 8.5), 50 mM KCl, 2.5 mM MgCl$_2$, 1 mM DTT, 0.05% CHAPS) is assayed in total volume of 20 μl containing 12.5 mM Glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 60 min after which 20 μl of ADP-Glo reagent is added. After a further incubation of 40 min, 40 µl of kinase detection Buffer is added. The assays are incubated for 40 min and then read on PerkinElmer Envision for 1 sec/well.

PI3K-δ Assay:

PI3K-delta (diluted in 12.5 mM Glycine-NaOH (pH 8.5), 50 mM KCl, 2.5 mM $MgCl_2$, 1 mM DTT, 0.05% CHAPS) is assayed in total volume of 20 µl containing 12.5 mM Glycine-NaOH (pH 8.5), 50 mM KCl, 2.5 mM $MgCl_2$, 1 mM DTT, 0.05% CHAPS, 0.01 mM ATP and 0.05 mM diC8 PIP2. The enzyme is assayed for 120 min after which 20 ul of ADP-Glo reagent is added. After a further incubation of 40 min, 40 µl of Kinase Detection Buffer is added. The assays are incubated for 40 min and then read on PerkinElmer Envision for 1 sec/well.

PI3K-γ Assay:

PI3K-gamma (diluted in 12.5 mM Glycine-NaOH (pH 8.5), 50 mM KCl, 2.5 mM $MgCl_2$, 1 mM DTT, 0.05% CHAPS) is assayed in total volume of 20 ul containing 12.5 mM glycine-NaOH (pH 8.5), 50 mM KCl, 2.5 mM $MgCl_2$, 1 mM DTT, 0.05% CHAPS, 0.01 mM ATP and 0.05 mM diC8 PIP2. The enzyme is assayed for 75 min after which 20 µl of ADP-Glo reagent is added. After a further incubation of 40 min, 40 µl of Kinase Detection Buffer is added. The assays are incubated for 40 min and then read on PerkinElmer Envision for 1 sec/well.

Example 28. Determination of Aqueous Solubility

The thermodyanamic aqueous solubility was determined using 96-plate plate protocol (Bharate, S. S. and Vishwakarma, R. A. 2015, Bioorg. Med. Chem. Lett. 25, 1561-1567). The dissolution media's PBS (pH 7.4), SGF (pH 1.2) and SIF (pH 6.8) were prepared as per USP procedure. Briefly, the compounds were loaded into 96-well plate in the form of methanolic solution, followed by evaporation of solvent to get 1, 2, 4, 8, 16, 25, 40, 80, 160 and 300 µg of compound in solid form in wells. Thereafter, 200 µl of dissolution medium was added to the wells and plates were shaken horizontally at 300 rpm for 4 h at room temperature (25±1° C.). The plates were covered with aluminium foil and were kept overnight at room temperature for equilibration. Later, the plates were centrifuged at 3000 rpm for 15 min (Jouan centrifuge BR4i). Supernatant (50 µl) was withdrawn into UV 96-well plates (Corning® 96 Well Clear Hat Bottom UV-Transparent Microplate) for analyses with microplate reader (Molecular Devices, USA) at corresponding $\lambda_{max}$ of the sample. The analysis was performed in triplicate for each compound. The solubility curve of concentration (µg/mL) vs absorbance was plotted to find out saturation point and the corresponding concentration was noted.

The results of preliminary kinase screening and their aqueous solubility data are shown in Table 1. Several fused pyrimidines showed >50% inhibition of PI3K-α at 0.5 µM except compounds 16, 26, 27, and 29. Compound 22 showed 74% inhibition of PI3K-α at 0.5 µM and showed excellent aqueous solubility (800 µg/ml). The $IC_{50}$ for PI3K-α inhibition was determined for best compounds 8, 10, and 22. Compound 22 displayed $IC_{50}$ of 40 nM for PI3K-α inhibition. Compound 22 was also tested for inhibition of other isoforms of PI3K. Results are shown in Table 2. It showed >500 fold selectivity for PI3K-α with respect to all other three isoforms—beta, gamma and delta. Whereas, the clinical candidate GDC-0941 and PI-103 are pan-PI3K inhibitors showing very poor selectivity and aqueous solubility. Compound 22 also possessed greater aqueous solubility than GDC-0941 and PI-103.

TABLE 1

Inhibition of phosphoinositide-3-kinase-α (PI3K-α) by fused pyrimidines and their aqueous solubility values

| Sr. No. | Compound | % PI3Kα inhibition at 500 nM | $IC_{50}$ for PI3Kα | Aqueous Solubility (µg/ml) at pH = 7 |
|---|---|---|---|---|
| 1 | 6 | 67.3 | nd | 10 |
| 2 | 8 | 85 | 8 nM | 10 |
| 3 | 10 | 76.8 | 80 nM | 400 |
| 4 | 16 | NI | nd | nd |
| 5 | 17 | 81 | nd | 200 |
| 6 | 21 | 59 | nd | 120 |
| 7 | 22 | 74 | 40 nM | 800 |
| 8 | 23 | 68 | nd | 20 |
| 9 | 24 | 70 | nd | nd |
| 10 | 25 | 76 | nd | 200 |
| 11 | 26 | 40 | nd | nd |
| 12 | 27 | 33 | nd | nd |
| 13 | 28 | 56 | nd | 20 |
| 14 | 29 | 21 | nd | nd |
| 15 | 30 | 54.8 | nd | 5 |

NI, no inhibition at tested concentration;
nd, not determined.

TABLE 2

Isoform selectivity data of compound 22 against other isoforms of phosphoinositide-3-kinase and its comparison with GDC-0941 and PI-103

| Compound | $IC_{50}$ for PI3K (µM) | | | | Fold-selectivity for PI3K-α with respect to other isoforms | | | Solubility µg/ml in $H_2O$ at pH = 7 |
|---|---|---|---|---|---|---|---|---|
| | PI3K-α | PI3K-β | PI3K-γ | PI3K-δ | PI3K-β | PI3K-γ | PI3K-δ | |
| 22 | 0.04 | >20 | >20 | >20 | >500 | >500 | >500 | 800 |
| GDC-0941 | 0.003 | 0.033 | 0.075 | 0.003 | 11 | 25 | 1 | 16 |
| PI-103 | 0.002 | 0.003 | 0.015 | 0.003 | 1.5 | 7.5 | 1.5 | 5 |

Example 29. Cytotoxicity of Compounds of the Invention

Selected compounds proposed in the present invention were evaluated for their cytotoxic effect against panel of 3 cancer cell line viz. MIAPaCa-2 (pancreatic cancer), A-549 (lung cancer), and MDA-MB-231 (breast cancer) using MTT assay. In each well of a 96-well plate, $3 \times 10^3$ cells were grown in 100 µL of medium. After 24 h, each test molecules were added to achieve a final concentration of 10 to 0.01 µmol/L, respectively. After 48 h of treatment, 20 µL of 2.5 mg/mL MTT (Organics Research, Inc.) solution in phosphate buffer saline was added to each well. After 48 h, supernatant was removed and formazan crystals were dissolved in 200 µL of DMSO. Absorbance was then measured at 570 nm using an absorbance plate reader (Bio-Rad Microplate Reader). Data are expressed as the percentage of viable cells in treated relative to non-treated conditions. Each experiment was repeated thrice and data was expressed as mean±SD of three independent experiments (Mordant, P. et al., *Mol. Cancer Ther.* 2010, 9, 358). Compounds showed promising cytotoxicity in panel of cell lines. Cytotoxicity results are shown in Table 3.

TABLE 3

Cytotoxicity of selected compounds in three cancer cell lines

| | $IC_{50}$ (µM) | | |
|---|---|---|---|
| Compound | MIAPaCa-2 (pancreatic) | A549 (lung) | MDA-MB-231 (breast) |
| 8 | 8 | 8 | 8 |
| 10 | 8 | 9 | 40 |
| 22 | 5 | 7 | 4 |
| 24 | 9 | 13 | 8 |

Example 30. In-Vivo Activity in Ehrlich Solid Tumor Model

Ehrlich ascites carcinoma (EAC) cells were collected from the peritoneal cavity of the swiss mice weighing 18-23 g, harbouring 8-10 days old ascitic tumor. $1 \times 10^7$ EAC cells were injected intramuscularly in the right thigh of swiss male mice selected for the experiment on day 0. The next day, animals were randomized and divided into different groups. Treatment groups (compound 22 and 5-fluorouracil) contained 7 animals each and control group contained 10 animals. Treatment groups were treated with compound 22 (25 mg/kg, i.p.) and 5-fluorouracil (22 mg/kg, i.p.) from day 1-9. The control group was similarly administered normal saline (0.2 ml, i/p) from day 1-9. On day 9 and 13, tumor bearing thigh of each animal was shaved and longest and shortest diameters of the tumor were measured with the help of vernier caliper. Tumor weight of each animal was calculated using the following formula.

$$\text{Tumor weight(mg)} = \frac{\text{Length (mm)} \times [\text{width (mm)}]^2}{2}$$

The percent tumor growth inhibition was calculated on day 13 by comparing the average values of treated groups with that of control group. Tumor growth in saline treated control animals was taken to be 100%. The results are summarized in Table 4. The compound 22 has shown promising activity at 25 mg/kg (i.p.) dose with 32.7% inhibition in tumor size compared to control. There is no mortality observed in the group treated with 22.

TABLE 4

In-vivo activity of 22 in Ehrlich solid tumor model

| | | | | Day 13 | | |
|---|---|---|---|---|---|---|
| | Avg. body weights (g) of animals on days | | | Avg. body | Avg. tumor weights | % Tumor Growth |
| Treatment groups | 1 | 5 | 9 | weights (g) | (mg) | Inhibition | Mortality |
| 22, 25 mg/kg, i.p. | 19.57 | 20.0 | 20.41 | 20.82 | 1128.4 | 32.73 | 0/7 |
| 5-Fluorouracil, 22 mg/kg, i/p) | 20.14 | 20.85 | 21.0 | 22.14 | 929.42 | 50.04 | 0/7 |
| Normal Control, 0.2 ml, i/p | 21.8 | 23.1 | 23.1 | 23.4 | 1860.4 | 0 | 0/10 |

ADVANTAGES OF THE INVENTION

The main advantages of the present invention are:
Compounds of the invention show excellent inhibition of phosphoinositide-3-kinase-alpha.
Compounds of the invention show excellent isoform selectivity for alpha-isoform.
Compounds of the invention show greater aqueous solubility.
Compounds of the invention are stable.

The invention claimed is:
1. A compound of formula A:

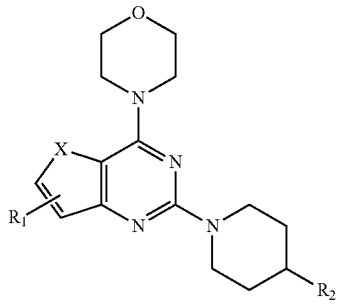

Formula A wherein,
X═ is O or S;
$R_1$ is selected from the group consisting of hydrogen, halogen, acetyl, alkylamino, nitro, sulfonyl, amino, aryl, heteroaryl, fused aryls, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl;
$R_2$ is selected from the

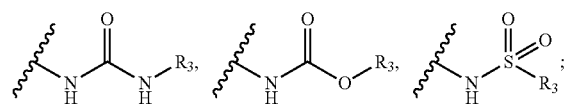

wherein, R₃ may be selected from H, alkoxy, substituted aryls, substituted heteroaryls, fused aryls, fused heteroaryls, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl;

aryl is selected from the group consisting of unsubstituted or substituted phenyl, fused aromatics, and substituted fused aromatics, wherein, substituents for phenyl are selected from the group consisting of methyl, nitro, halogens, formyl, vinyl, benzyl, acetyl, hydroxy, phenyl, benzamides, alkylphenyls, and alkoxyphenyls.

2. The compound as claimed in claim 1, wherein the compound of Formula A comprising of formula I and II:

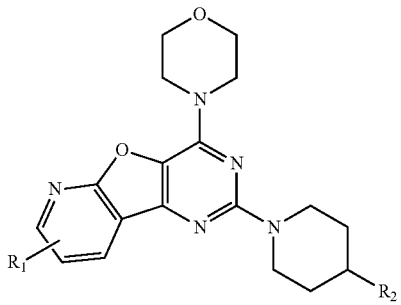

I

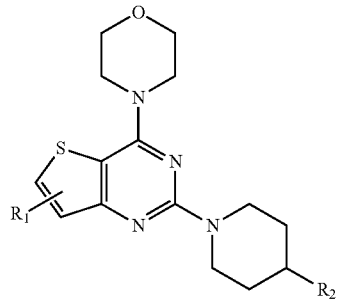

II wherein,

X is selected from the group consisting of O or S;

R₁ is selected from the group consisting of hydrogen, halogen, acetyl, alkylamino, nitro, sulfonyl, amino, aryl, heteroaryl, fused aryls, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl;

R₂ is selected from the

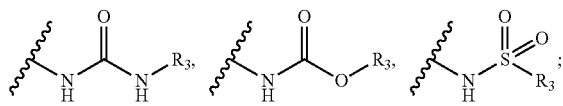

wherein, R₃ may be selected from H, alkoxy, substituted aryls, substituted heteroaryls, fused aryls, fused heteroaryls, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl;

aryl is selected from the group consisting of unsubstituted or substituted phenyl, fused aromatics and substituted fused aromatics, wherein, substituents for phenyl are selected from the group consisting of methyl, nitro, halogens, formyl, vinyl, benzyl, acetyl, hydroxy, phenyl, benzamides, alkylphenyls, and alkoxyphenyls.

3. The compound as claimed in claim 1, wherein the representative compound of the Formula A is:

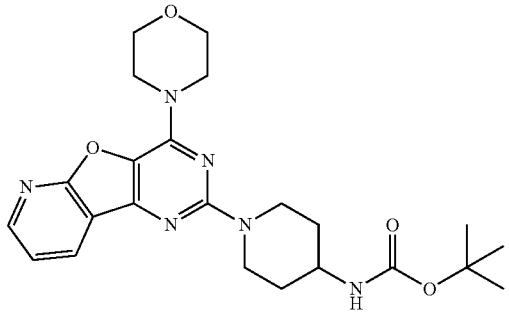 [SMILES: CC(C)(C)OC(=O)NC1CCN(c2nc(N3CCOCC3)c3oc4ncccc4c3n2)CC1]

tert-butyl (1-(4-morpholinopyrido [3',2':4,5]furo[3,2-d]pyrimidin-2-yl)piperidin-4-yl)carbamate (6),

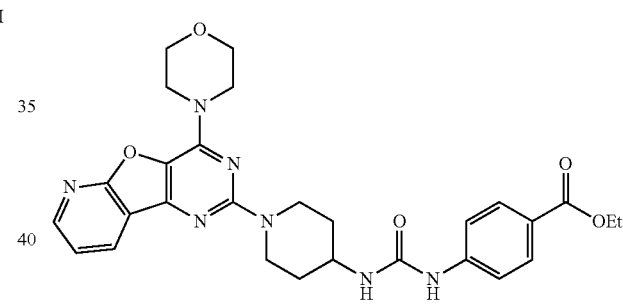

ethyl 4-(3-(1-(4-morpholinopyrido[3',2':4,5]furo[3,2-d]pyrimidin-2-yl)piperidin-4-yl)ureido)benzoate, (8),

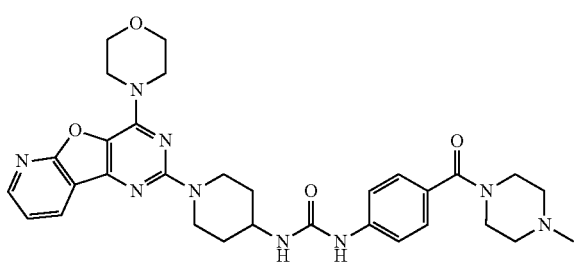 [SMILES: CN1CCN(C(=O)c2ccc(NC(=O)NC3CCN(c4nc(N5CCOCC5)c5oc6ncccc6c5n4)CC3)cc2)CC1]

1-(4-(4-methylpiperazine-1-carbonyl)phenyl)-3-(1-(4-morpholinopyrido[3',2':4,5]furo[3,2-d]pyrimidin-2-yl)piperidin-4-yl)urea (10),

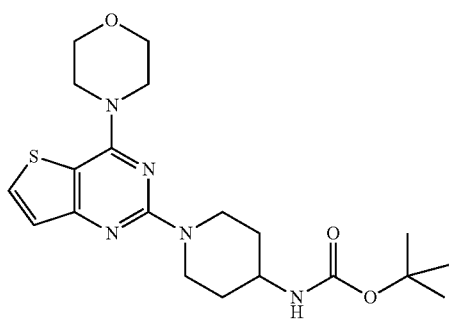 [SMILES: CC(C)(C)OC(=O)NC1CCN(c2nc(N3CCOCC3)c3sccc3n2)CC1]

tert-butyl (1-(4-morpholino thieno[3,2-d]pyrimidin-2-yl)piperidin-4-yl)carbamate (16),

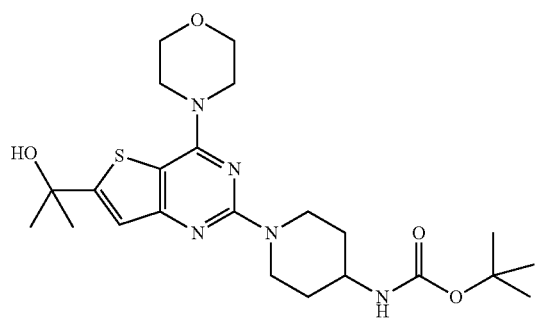 [SMILES: CC(C)(C)OC(=O)NC1CCN(c2nc(N3CCOCC3)c3sc(C(C)(C)O)cc3n2)CC1]

tert-butyl (1-(6-(2-hydroxypropan-2-yl)-4-morpholinothieno[3,2-d]pyrimidin-2-yl)piperidin-4-yl)carbamate (17),

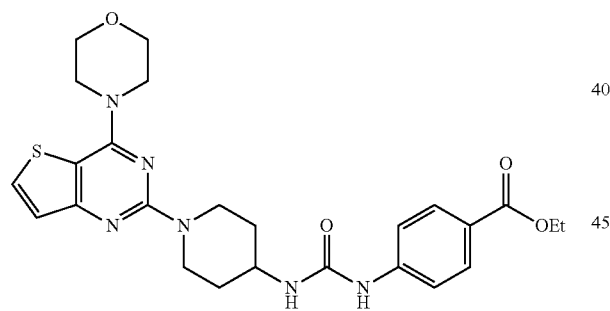

ethyl 4-(3-(1-(4-morpholino thieno[3,2-d]pyrimidin-2-yl)piperidin-4-yl)ureido)benzoate (21),

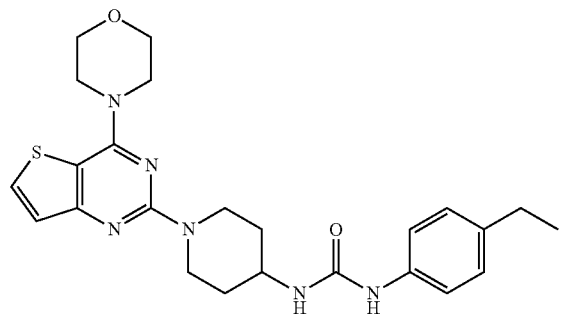 [SMILES: CCc1ccc(NC(=O)NC2CCN(c3nc(N4CCOCC4)c4sccc4n3)CC2)cc1]

1-(4-ethylphenyl)-3-(1-(4-morpholinothieno[3,2-d]pyrimidin-2-yl)piperidin-4-yl)urea (22),

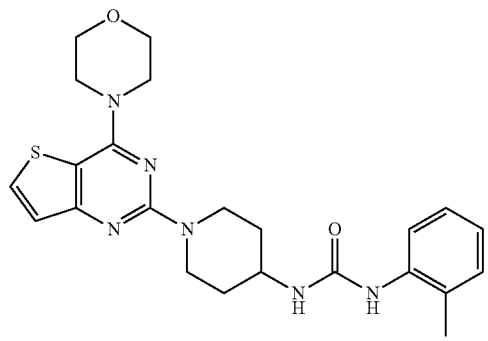 [SMILES: Cc1ccccc1NC(=O)NC1CCN(c2nc(N3CCOCC3)c3sccc3n2)CC1]

1-(1-(4-morpholinothieno[3,2-d]pyrimidin-2-yl)piperidin-4-yl)-3-(o-tolyl)urea (23),

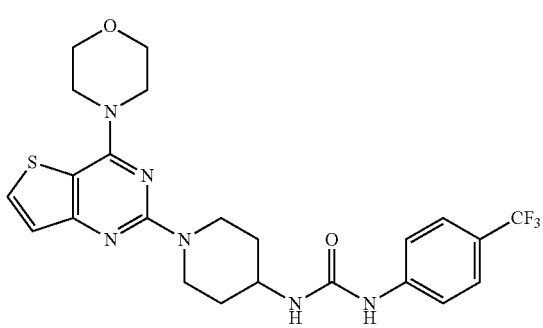 [SMILES: O=C(Nc1ccc(C(F)(F)F)cc1)NC1CCN(c2nc(N3CCOCC3)c3sccc3n2)CC1]

1-(1-(4-morpholinothieno[3,2-d]pyrimidin-2-yl)piperidin-4-yl)-3-(4-(trifluoromethyl)phenyl)urea (24),

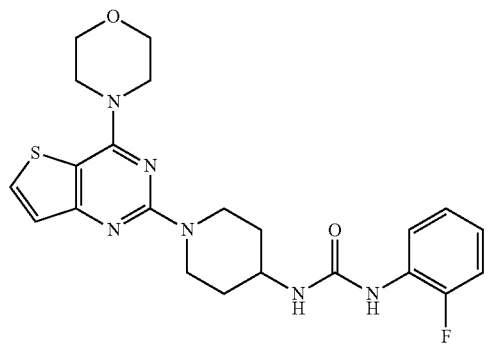 [SMILES: O=C(Nc1ccccc1F)NC1CCN(c2nc(N3CCOCC3)c3sccc3n2)CC1]

1-(2-fluorophenyl)-3-(1-(4-morpholinothieno[3,2-d]pyrimidin-2-yl)piperidin-4-yl)urea (25),

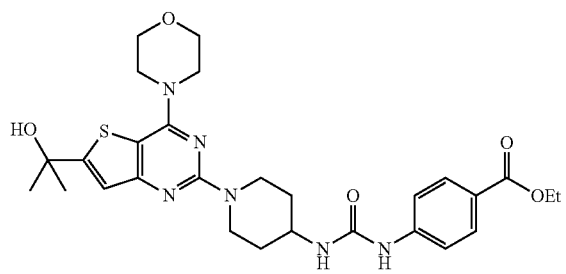 [SMILES: CCOC(=O)c1ccc(NC(=O)NC2CCN(c3nc(N4CCOCC4)c4sc(C(C)(C)O)cc4n3)CC2)cc1]

ethyl 4-(3-(1-(6-(2-hydroxypropan-2-yl)-4-morpholinothieno[3,2-d]pyrimidin-2-yl)piperidin-4-yl)ureido)benzoate (26),

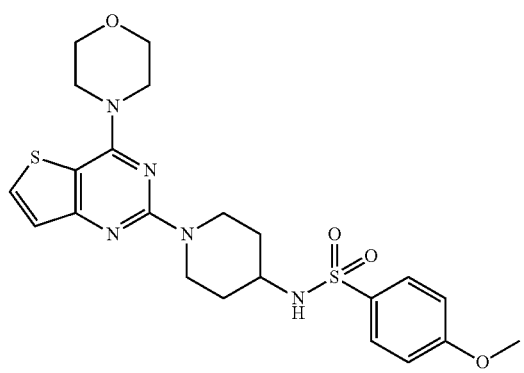 [SMILES: COc1ccc(S(=O)(=O)NC2CCN(c3nc(N4CCOCC4)c4sccc4n3)CC2)cc1]

4-methoxy-N-(1-(4-morpholinothieno[3,2-d]pyrimidin-2-yl)piperidin-4-yl)benzenesulfonamide (27),

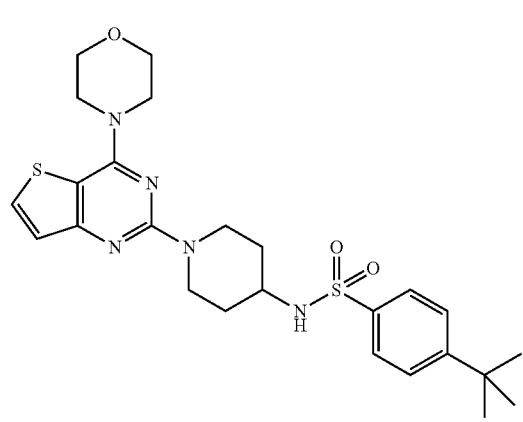 [SMILES: CC(C)(C)c1ccc(S(=O)(=O)NC2CCN(c3nc(N4CCOCC4)c4sccc4n3)CC2)cc1]

4-(tert-butyl)-N-(1-(4-morpholinothieno[3,2-d]pyrimidin-2-yl)piperidin-4-yl)benzenesulfonamide (28),

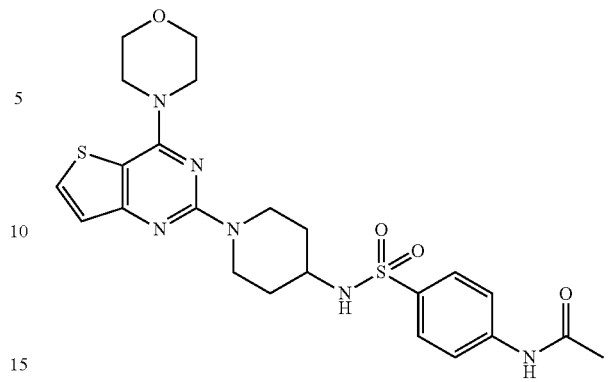

N-(4-(N-(4-(4-morpholino thieno[3,2-d]pyrimidin-2-yl)cyclohexyl) sulfamoyl) phenyl) acetamide (29) or

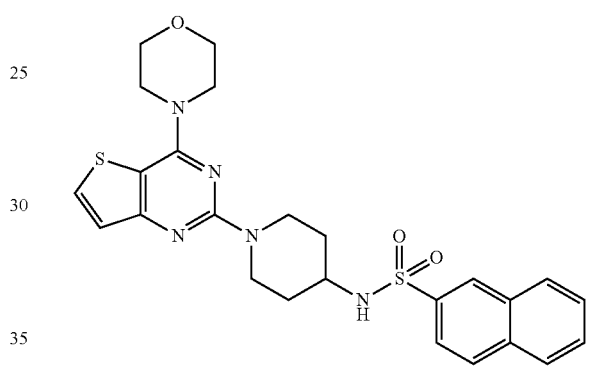

N-(1-(4-morpholino thieno[3,2-d]pyrimidin-2-yl)piperidin-4-yl)naphthalene-2-sulfonamide (30).

4. The compound as claimed in claim 1, wherein the compounds are useful for the treatment of cancer.

5. The compound as claimed in claim 1, wherein the compounds are phosphoinositide-3-kinase inhibitors.

6. The compound as claimed in claim 1, wherein, the compounds are PI3K-α inhibitors and inhibits up to about 85% at 0.5 μM concentration.

7. A process for preparation of the compound of general formula A, wherein the process steps comprising of:

a) reacting tert-butyl piperidin-4-yl-carbamate in a solvent with compound Ia followed by addition of a base, and then reflux at 140-150° C. for 8-10 h to obtain compound IIa:

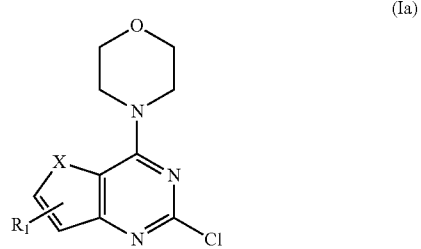

(Ia)

-continued (IIa)

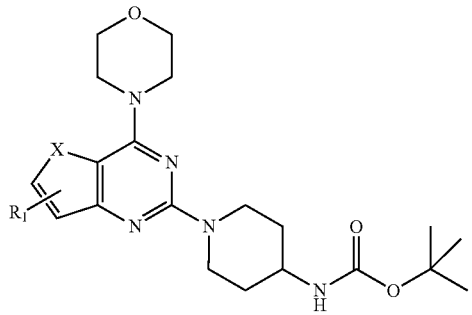

wherein, X is O or S;

R₁ is selected from the group consisting of hydrogen, halogen, acetyl, alkyl, alkylamino, -nitro, sulfonyl, amino, aryl, heteroaryl, or fused aryls;

b) wherein alkyl group is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl, treating compound IIa obtained from step (a) with 30% TFA in DCM or chloroform for a period in the range of 1 to 5 h to obtain compound IIIa:

(IIIa)

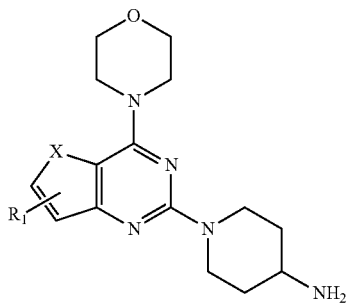

wherein,

X is O or S;

R₁ is selected from the group consisting of hydrogen, halogen, acetyl, alkylamino, nitro, sulfonyl, amino, aryl, heteroaryl, fused aryls; wherein Alkyl group is selected from the group consisting of, ($C_1$-$C_6$)-alkyl, ($C_1$-$C_4$)-haloalkyl, ($C_1$-$C_4$)-alkoxy, ($C_1$-$C_4$)-haloalkoxy; ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl;

c) reacting ethyl 4-isocyanatobenzoate with compound IIIa obtained from step (f) in a solvent in presence of a base for a period in the range of 1 to 5 h at a temperature ranging between 25 to 40° C. to obtain compound IVa:

(IVa)

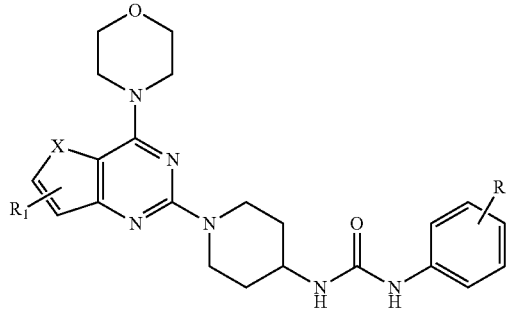

wherein,

X is O or S;

R₁ is selected from the group consisting of hydrogen, halogen, acetyl, alkylamino, nitro, sulfonyl, amino, aryl, heteroaryl, fused aryls, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl, and ($C_6$-$C_{10}$)-bicycloalkenyl; wherein, R= is selected from 4-COOEt, 4-Et, 2-Me, 4-CF₃ or 2-F COOH;

d) reacting compounds IIIa obtained from step (f) with sulfonyl chlorides in a solvent in presence of a base for a period in the range of 6 to 10 h at a temperature ranging between 25 to 40° C. to obtain compound Va:

(Va)

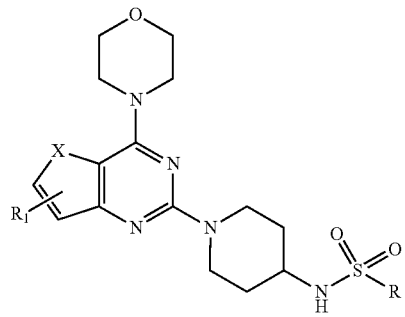

wherein,

X is O or S;

R₁ is selected from the group consisting of hydrogen, halogen, acetyl, alkylamino, nitro, sulfonyl, amino, aryl, heteroaryl, fused aryl, ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl, wherein, R= is selected from Ph(4-OMe), Ph(4-t-Bu), Ph(4-acetamido) or napthalen-2-yl.

8. The process as claimed in claim 7, wherein the solvent used in step (c) and (d) is selected from the group consisting of DCM or chloroform.

9. The process as claimed in claim 7, wherein the base used in step (a), (c) and (d) is selected from the group consisting of Et₃N, K₂CO₃, or Cs₂CO₃.

* * * * *